(12) United States Patent
Hoshino et al.

(10) Patent No.: US 8,113,055 B2
(45) Date of Patent: Feb. 14, 2012

(54) METHOD FOR EVALUATING FASTENING STATE OF THREADED JOINT OF PIPES OR TUBES AND METHOD FOR FASTENING THREADED JOINT OF PIPES OR TUBES USING THE METHOD

(75) Inventors: Ikuji Hoshino, Osaka (JP); Masaki Yamano, Osaka (JP); Shigeo Nagasaku, Osaka (JP)

(73) Assignees: Sumitomo Metal Industries, Ltd., Osaka (JP); Vallourec Mannesmann Oil & Gas France, Aulnoye-Aymeries (FR)

( * ) Notice: Subject to any disclaimer, the term of this patent is extended or adjusted under 35 U.S.C. 154(b) by 84 days.

(21) Appl. No.: 12/310,799

(22) PCT Filed: Sep. 6, 2007

(86) PCT No.: PCT/JP2007/067892
§ 371 (c)(1),
(2), (4) Date: Jul. 2, 2009

(87) PCT Pub. No.: WO2008/029957
PCT Pub. Date: Mar. 13, 2008

(65) Prior Publication Data
US 2009/0282921 A1    Nov. 19, 2009

(30) Foreign Application Priority Data

Sep. 7, 2006  (JP) ................................ 2006-242566
Mar. 26, 2007  (JP) ................................ 2007-078377

(51) Int. Cl.
*G01N 29/11*  (2006.01)
*G01N 29/48*  (2006.01)
*G01N 29/36*  (2006.01)
(52) U.S. Cl. ............................... 73/600; 73/622
(58) Field of Classification Search ................. 73/599, 73/600, 622, 625, 626, 628
See application file for complete search history.

(56) References Cited

U.S. PATENT DOCUMENTS 4,870,866 A * 10/1989 Slack ................................ 73/599
(Continued)

FOREIGN PATENT DOCUMENTS

JP           61-187648            8/1986
(Continued)

OTHER PUBLICATIONS

A. Narita et al., "Sumitomo's Premium Connection "VAM ACE" for OCTG", Sumitomo Metals, Jan. 1994, vol. 46, No. 1, pp. 65-73.

*Primary Examiner* — Hezron E Williams
*Assistant Examiner* — Rose M Miller
(74) *Attorney, Agent, or Firm* — Clark & Brody

(57) ABSTRACT

There is provided a method capable of evaluating a fastening state of a threaded joint that is used as a joint of pipes or tubes such as OCTG with a high degree of accuracy even after being fastened and a method for fastening a threaded joint of pipes or tubes using the evaluating method. The present invention provides a method for evaluating a fastening state of a threaded joint of pipes or tubes including a pin having an external thread part, a metal seal part, and a shoulder part on an outer peripheral surface, and a box having an internal thread part, a metal seal part, and a shoulder part corresponding to each part of the pin on an inner peripheral surface and being fastened with the pin. The evaluating method according to the present invention is characterized by transmitting and receiving an ultrasonic wave to and from a plurality of locations along an axial direction of the threaded joint in at least one of the internal thread part, the metal seal part, and the shoulder part of the box; detecting echo intensities for the plurality of locations; and comparing the echo intensities detected for the plurality of locations to determine whether the fastening state of the threaded joint is good or bad.

5 Claims, 23 Drawing Sheets

U.S. PATENT DOCUMENTS

| | | | |
|---|---|---|---|
| 6,438,814 B1 * | 8/2002 | Seymour et al. | 29/407.02 |
| 2005/0256676 A1 * | 11/2005 | Ales et al. | 702/159 |

FOREIGN PATENT DOCUMENTS

| | | | |
|---|---|---|---|
| JP | 63298054 A * | 12/1988 | |
| JP | 1-235848 | 9/1989 | |
| JP | 1-235848 A * | 9/1989 | |
| JP | 9-152425 | 6/1997 | |
| JP | 2001-108662 | 4/2001 | |
| SU | 905778 B * | 2/1982 | |

* cited by examiner

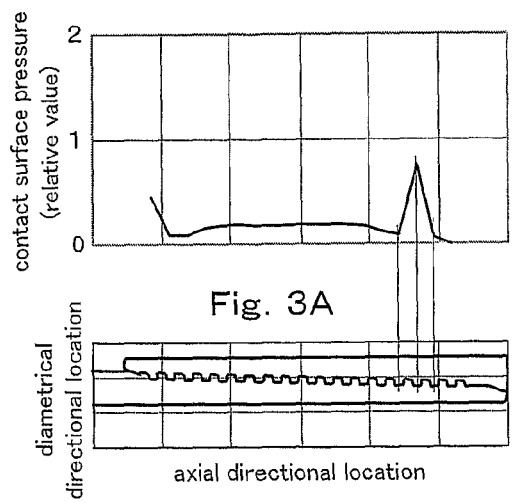
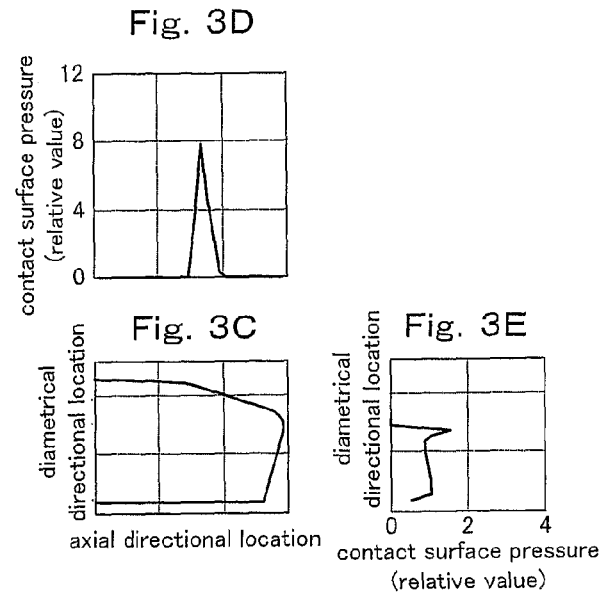

axial directional location (mm)

axial directional location (mm)

axial directional location (mm)

axial directional location (mm)

<evaluation index>
(1) X/(A+B)
(2) X/A
(3) X/B

<evaluation method>
if evaluation index ≤ Th, then fastening state is good.
if evaluation index > Th, then fastening state is bad.

X: intensity of echo having minimum intensity (evaluated)
A: intensity of echo in adjacent to top side (standard)
B: intensity of echo in adjacent to bottom side (standard)
Th: threshold value ⟨evaluation index⟩
  X/A ⟨evaluation method⟩
  if evaluation index ≤ Th, then fastening state is good.
  if evaluation index > Th, then fastening state is bad.

X: intensity of echo near center portion of seal face (evaluated)
  A: intensity of echo of end portion on bottom side of seal face (standard)
  Th: threshold value <evaluation index>
   X/A <evaluation method>
   if evaluation index ≤ Th, then fastening state is good.
   if evaluation index > Th, then fastening state is bad.

X: corner echo intensity (evaluated)
   A: intensity of echo of end portion on bottom side of seal face (standard)
   Th: threshold value axial directional location (mm)

circumferential directional location (°)

echo intensity (%)

METHOD FOR EVALUATING FASTENING STATE OF THREADED JOINT OF PIPES OR TUBES AND METHOD FOR FASTENING THREADED JOINT OF PIPES OR TUBES USING THE METHOD

BACKGROUND OF THE INVENTION

1. Field of the Invention

The present invention relates to a method for evaluating a fastening state of a threaded joint that is used as a joint of pipes or tubes such as Oil Country Tubular Goods (OCTG) with a high degree of accuracy not only during being fastened but also after being fastened and a method for fastening a threaded joint of pipes or tubes using the evaluating method. Hereinafter, "pipes or tubes" are referred to as "pipes" when deemed appropriate.

2. Description of the Related Art

Conventionally, as a joint for OCTG, a threaded joint has been widely used. FIG. 1 is an axial directional cross sectional view that schematically illustrates a general structure of a threaded joint. As shown in FIG. 1, a threaded joint 100 is provided with a pin 1 having an external thread part 11, a metal seal part 12, a shoulder part 13 on an outer peripheral surface, and a box 2 having an internal thread part 21, a metal seal part 22, and a shoulder part 23 corresponding to each part of the pin 1 on an inner peripheral surface and being fastened with the pin 1.

The external thread part 11 and the internal thread part 21 (hereinafter, these parts are generally named as "thread parts 11, 21") are screwed with each other so as to effect a function for fastening the pin 1 and the box 2. The external diameter of the metal seal part 12 is slightly larger than the internal diameter of the metal seal part 22 (this difference is referred to as "an interference margin"), and when the pin 1 is fastened with the box 2, due to the interference margin, a surface pressure is generated on a contact region between the both metal seal parts 12, 22 and due to this contact surface pressure, a function to sufficiently hold an air leakage efficiency of the threaded joint 100 is effected. The shoulder parts 13, 23 effect a function to prevent a high contact surface pressure such that an excess plastic transformation is generated from being generated on the metal seal parts 12, 22 and secure sufficient screwing amount so as to ascertain fastening of the threaded joint 100. Further, not only on the metal seal parts 12, 22 but also on the thread parts 11, 21, the threaded joint 100 may have the same interference margin as the metal seal parts 12, 22 in order to secure screwing of the thread parts 11, 21 so that they are not easily loosened. In this case, the shoulder parts 13, 23 also effect a function to limit the interference margins of the thread parts 11, 21 into a safe area so as to prevent an excess stress on the box 2.

As a method for evaluating a fastening state of a threaded joint having the above-described structure, conventionally, a method for monitoring change of a torque to be generated when fastening a threaded joint has been widely used (for example, refer to Japanese Patent Application Laid-Open No. 10-267175). FIG. 2 is an explanatory view for explaining a conventional method for evaluating a fastening state of a threaded joint. As shown in FIG. 2, as fastening of the threaded joint has been progressed in series, due to a frictional resistance due to interference of the thread parts 11, 21 and interference of the metal seal parts 12, 22, a torque is generated. Then, due to abutting of the shoulder parts 13, 23, the torque rapidly rises. Conventionally, good and bad of the fastening state of the threaded joint is determined by monitoring this change of the torque by an operator. In other words, in the case that the torque rises more than a predetermined threshold value, judging that the shoulder parts 13, 23 abut against with each other, it is determined that the fastening of the threaded joint 100 has been sufficiently completed.

However, according to the conventional evaluating method shown in FIG. 2, the fact that the thread parts 11, 21 interfere with each other, the metal seal parts 12, 22 interfere with each other, and the shoulder parts 13, 23 abut against with each other in face is not evaluated by measuring any physical amount independently and respectively. This is absolutely a method based on a past empirical rule such that a torque is generated because respective parts adhere tightly (interfere or abut) with each other. It is true that a torque is generated when respective parts adhere tightly (interfere or abut) with each other, however, a large torque is also generated due to other case, for example, when the thread parts 11, 21 are burnt or the like. Therefore, only by monitoring change of the torque, it is difficult to evaluate the fastening state with a high degree of accuracy.

In addition, the conventional evaluating method shown in FIG. 2 is restricted such that it is necessary to continuously monitor a torque in a process for fastening the threaded joint (in the middle of fastening a pin and a box while they are relatively moving). In other words, the conventional evaluating method is restricted such that the fastening state cannot be evaluated when the pin and the box stand still after fastening them.

SUMMARY OF THE INVENTION

The present invention has been made taking the foregoing problems into consideration and an object of which is to provide a method for evaluating a fastening state of a threaded joint that is used as a joint of pipes such as OCTG with a high degree of accuracy not only during being fastened but also after being fastened and a method for fastening a threaded joint of pipes using the evaluating method.

In order to solve the above-described object, as a result of concentration of consideration, the inventors obtain the following knowledge.

(1) A contact surface pressure between each part of the pin (an external thread part, a metal seal part, and a shoulder part) and each part of the box (an internal thread part, a metal seal part, and a shoulder part) is changed in accordance with the fastening states of these respective parts. Specifically, with respective parts of the pin and the box adhering tightly with each other, as compared to the state that they do not adhere tightly, a contact surface pressure may be higher.

(2) However, change of the contact surface pressure of (1) is not even across an entire area of each part and the contact surface pressure is locally changed along an axial direction of a threaded joint. Specifically, with respective parts adhering tightly with each other, the contact surface pressure may be locally higher as compared to the state that they do not adhere tightly.

(3) The contact surface pressure and an echo intensity of an ultrasonic wave have a relative relation. Specifically, the echo intensity of the ultrasonic wave that is received from a location having a high contact surface pressure is lower than that of the ultrasonic wave that is received from a location having a low contact surface pressure.

The present invention has been completed on the basis of the above-described knowledge of the inventors. The present invention provides a method for evaluating a fastening state of a threaded joint of pipes or tubes including a pin having an external thread part, a metal seal part, and a shoulder part on an outer peripheral surface, and a box having an internal thread part, a metal seal part, and a shoulder part corresponding to each part of the pin on an inner peripheral surface and being fastened with the pin, the method comprising the steps of: transmitting and receiving ultrasonic waves to and from a plurality of locations along an axial direction of the threaded joint in at least one of the internal thread part, the metal seal part, and the shoulder part of the box; detecting echo intensities for the plurality of locations; and comparing the echo intensities detected for the plurality of locations to determine whether the fastening state of the threaded joint is good or bad.

According to the present invention, ultrasonic waves are transmitted and received to and from a plurality of locations along an axial direction of a threaded joint in at least one part among an external thread part, a metal seal part, and a shoulder part of a box forming a threaded joint (hereinafter, appropriately referred to as "a part to be evaluated"). As described above, the contact surface pressure between respective parts of the pin and respective parts of the box corresponding to the respective parts of the pin may be locally higher along the axial direction of the threaded joint as adhering tightly with each other and at the same time, the echo intensity of the ultrasonic wave that is received from the location having a high contact surface pressure is lower than that of the ultrasonic wave that is received from the location having a low contact surface pressure. Accordingly, if the ultrasonic waves are transmitted and received to and from a plurality of locations along the axial direction of the threaded joint in each part of the box, when each part of the box adheres tightly with each part of the pin, the echo intensity of the ultrasonic wave received from the location where the contact surface pressure is locally higher is lower, and at the same time, on the remaining locations where the contact surface pressure is low, the echo intensity of the ultrasonic wave is large. On the other hand, with respective parts of the box not adhering tightly with respective parts of the pin, since there is no location where the contact surface pressure is locally higher on each part of the box, the echo intensity of the ultrasonic wave is large across the entire area of each part.

Therefore, comparing the echo intensities that are detected for the plural locations, it is possible to determine good and bad of the fastening state of the threaded joint. Specifically, for example, detecting the echo intensities for the plural locations of the part to be evaluated, respectively, if a rate between the minimum value and the maximum value of the detected echo intensities (the minimum value/the maximum value) is not more than a predetermined threshold value, the part to be evaluated of the box adheres tightly with the part of the pin corresponding to this, so that it is possible to determine that this fastening state is satisfactory. On the other hand, if a rate between the minimum value and the maximum value of the detected echo intensity is larger than a predetermined threshold value, the part to be evaluated of the box does not adhere tightly with the part of the pin corresponding to this, so that it is possible to determine that this fastening state is unsatisfactory (including the case that fastening has not been completed).

According to the evaluating method of the present invention, the echo intensities having a relative relation in a contact surface pressure between each part of a pin and each part of a box corresponding to this is detected independently for each part. Therefore, a contact surface pressure of each part and further, a fastening state of each part can be evaluated on the basis of this detected echo intensities. According to the conventional method for monitoring change of a torque, it is not exactly known in what part the fastening state contributes to change of a torque and there is a possibility that other cause such as burning may contribute to change of the torque. As compared to this conventional method, the evaluating method of the present invention can be expected to make evaluation with a high degree of accuracy. In addition, since the evaluating method according to the present invention may evaluate the fastening state on the basis of the contact surface pressure (namely, on the basis of the echo intensity of the ultrasonic wave having a relative relation with the contact surface pressure), evaluating the fastening state (in the middle of fastening the pin and the box while they are relatively moving) in the process of fastening the threaded joint is not an essential condition differently from a conventional case and the evaluation is available not only when the pin and the box are fastening but also when the fastened pin and box stand still.

Further, since the evaluating method according to the present invention may compare the echo intensities for a plurality of locations in the same part of the box (for example, a plurality of locations of the metal seal part of the box), the evaluating method according to the present invention has an advantage such that an evaluation result hardly has an effect from variation of an absolute value of the echo intensity. The absolute value of the echo intensity is varied depending on the contact state of an ultrasonic probe for transmitting and receiving the ultrasonic wave and the surface state of the box and the pin or the like, so that according to the method for determining good and bad of the fastening state simply on the basis of the absolute value of the echo intensity (for example, according to the method for determining if the fastening state is not good if the minimum value of the detected echo intensities exceeds a predetermined threshold value), a degree of accuracy of a determination result is deteriorated. In addition, a method for comparing the echo intensities before and after fastening of the same part of the box (for example, a method for determining that the fastening state is not good if a rate between the minimum value of the echo intensities that are detected after fastening and the minimum value of the echo intensities that are detected before fastening exceeds a predetermined value) may be also considered, however, in order to apply this method, it is necessary to make the detection condition such as a contact state of an ultrasonic probe or the like substantially the same when detecting the echo intensities before and after fastening, respectively. However, it is very difficult to make the detection conditions of the echo intensities the same before and after fastening in fact. The evaluating method according to the present invention also has an advantage in that it is enough to detect the echo intensities during fastening or after fastening of the threaded joint without receiving a restriction such that the detection conditions of the echo intensities are made the same before and after fastening of the threaded joint.

Here, if a frequency of an ultrasonic wave (a test frequency) to be transmitted or received is made excessively high, it becomes difficult for the ultrasonic wave to transmit toward the pin whether or not the fastening state of each part of the box and the pin corresponding to this. In other words, even if the contact surface pressure between each part of the box and each part of the pin corresponding to this is changed, the echo intensity of the ultrasonic wave is hardly changed, so that this is not preferable for determination of good and bad of the fastening state. Accordingly, it is preferable that a frequency of an ultrasonic wave to be transmitted and received is set to be not more than 25 MHz (more preferably, not more than 5 MHz).

Further, as a method for transmitting and receiving ultrasonic waves to and from a plurality of locations along an axial direction of a threaded joint for at least one part of the box, for example, a method for relatively moving an ultrasonic probe along the axial direction of the threaded joint may be recited.

Alternatively, it is also possible to employ a method for electrically controlling transmission and reception of an ultrasonic wave by to each transducer of an ultrasonic phased array probe in which a plurality of transducers are arrayed in one row.

Further, the present invention is also provided as a method for fastening a threaded joint of pipes, which is characterized by determining good and bad of the fastening state of the threaded joint by using the evaluating method in the fastening process of the threaded joint, and when the determination result becomes good, terminating fastening of the threaded joint.

According to the method for evaluating the fastening state of the threaded joint, an excellent advantage is realized such that the fastening state of the threaded joint that is used as a joint of pipes such as OCTG with a high degree of accuracy not only during being fastened but also after being fastened.

BRIEF DESCRIPTION OF THE DRAWING(S)

Figure 4A:
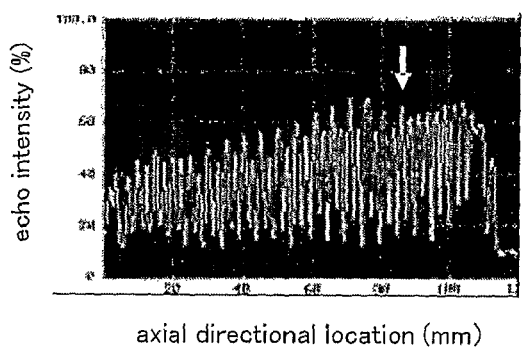
Figure 4B:
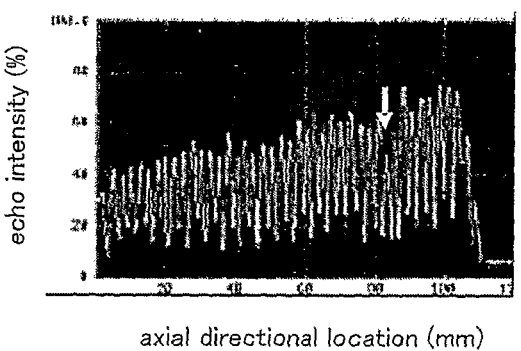
Figure 5A:
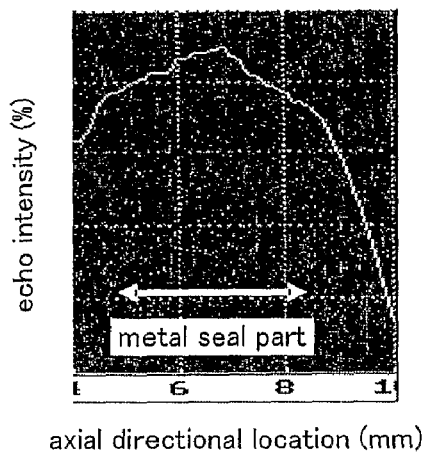
Figure 5B:
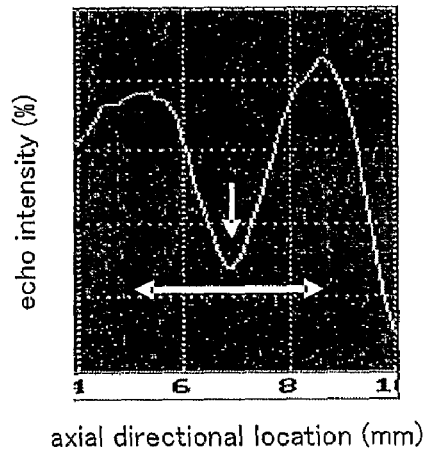
Figure 6A:
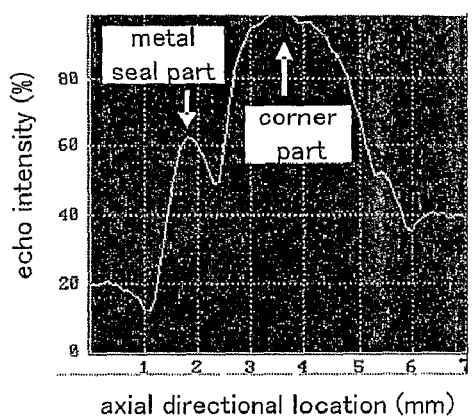
Figure 6B:
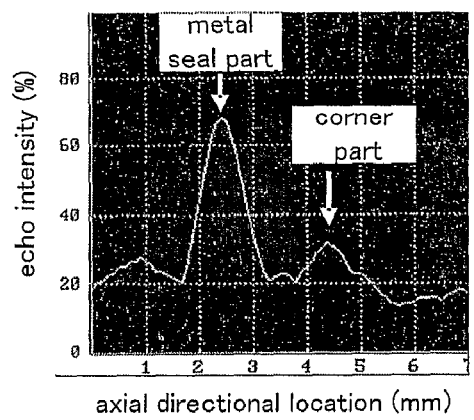
Figure 7:
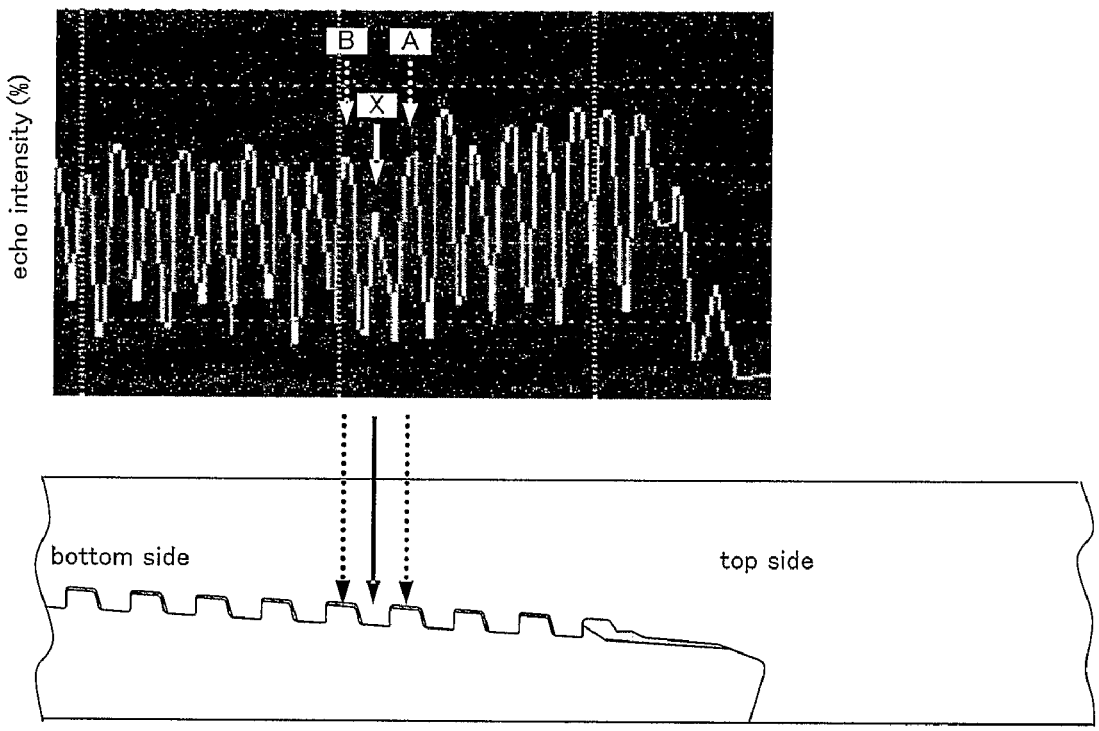
Figure 8:
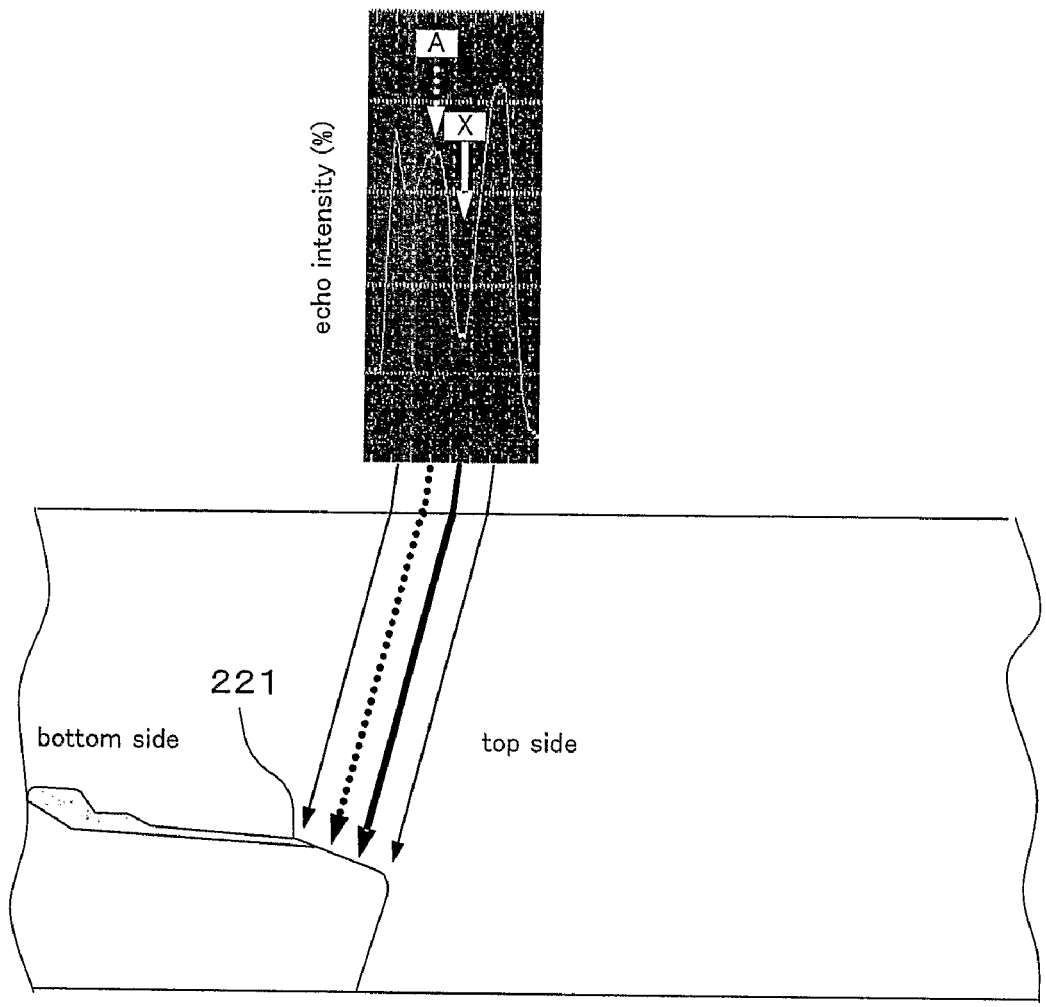
Figure 9:
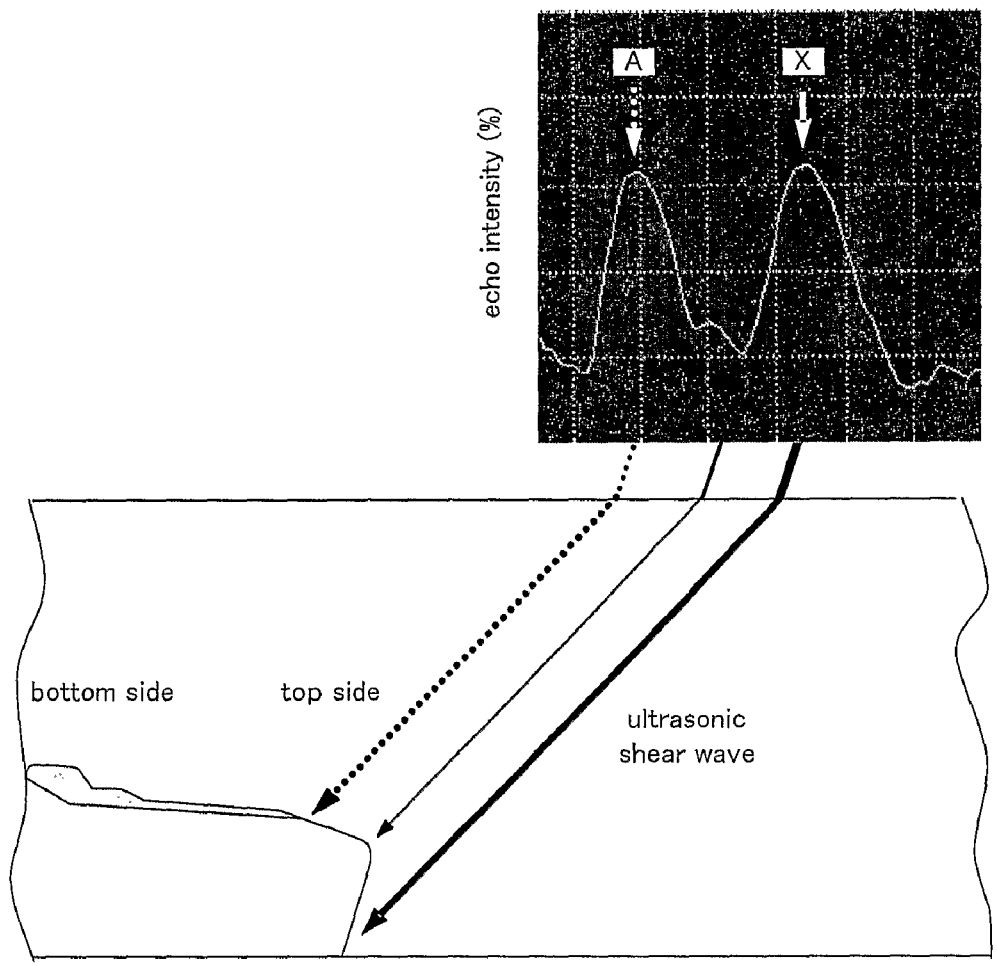
Figure 10A:
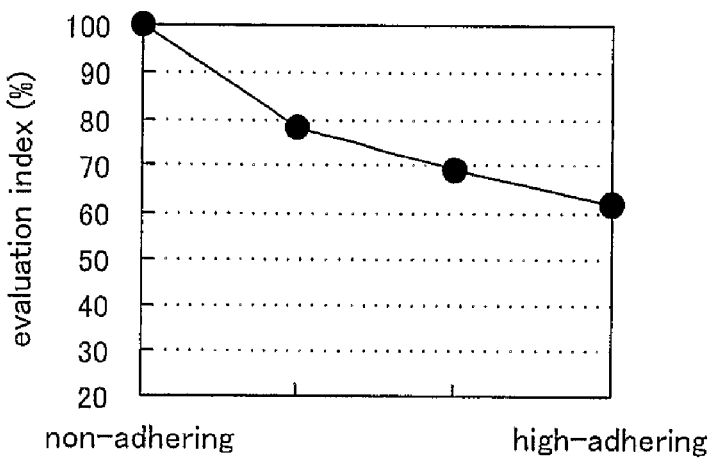
Figure 10B:
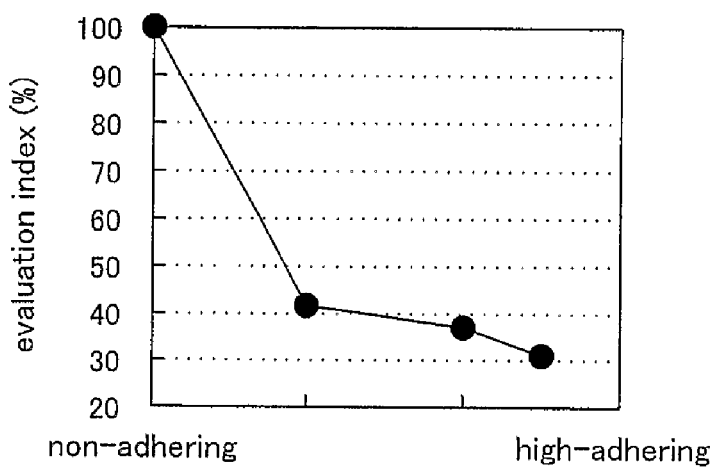
Figure 10C:
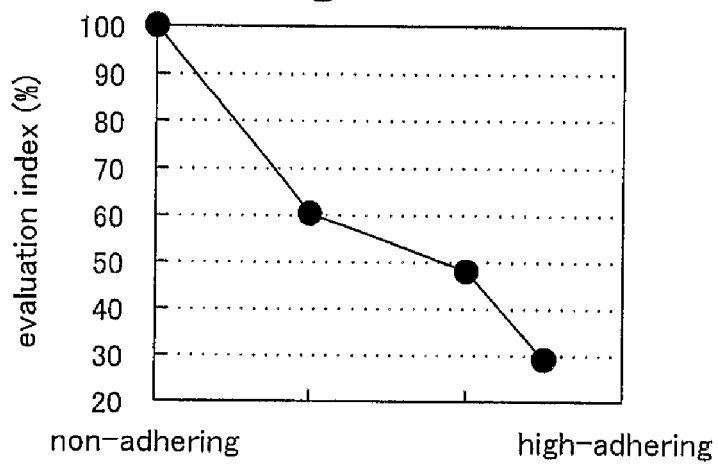
Figure 11:
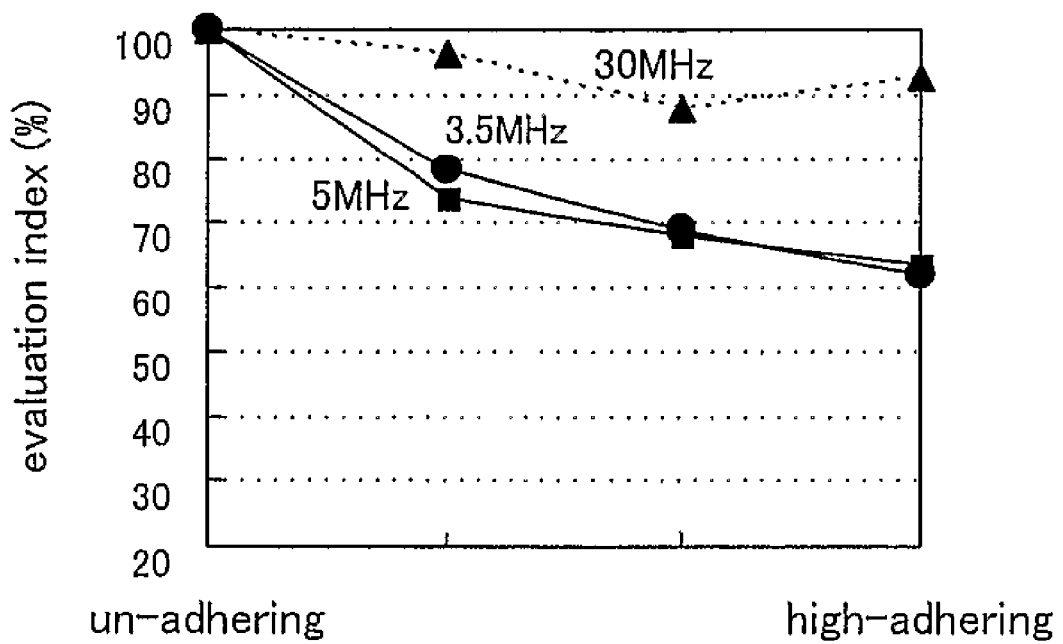
Figure 12:
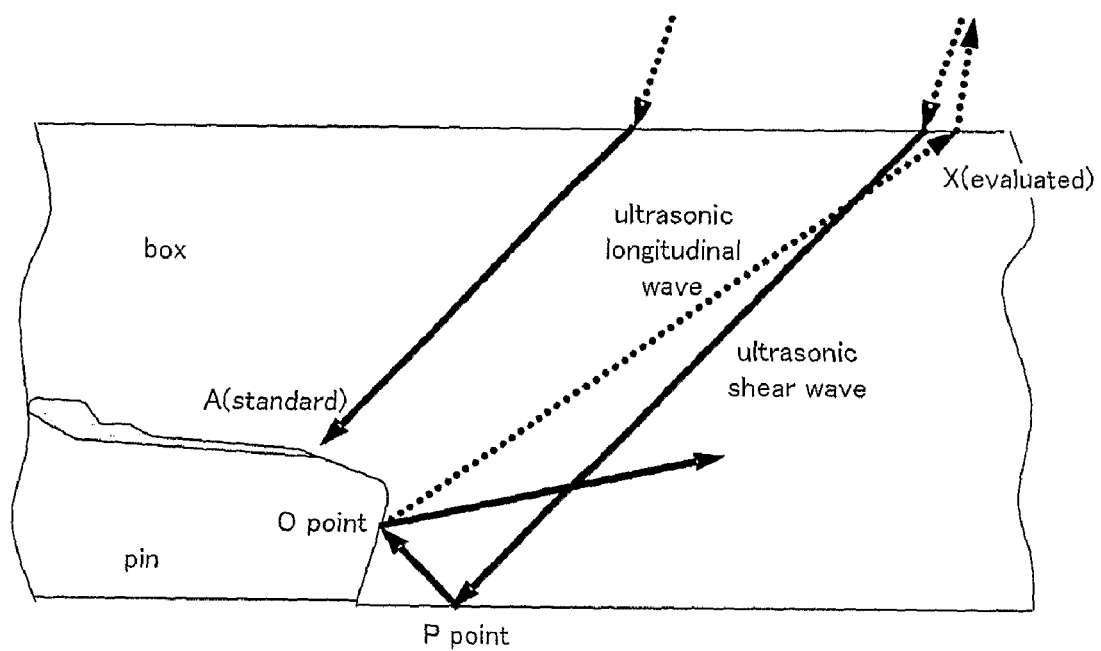
Figure 13A:
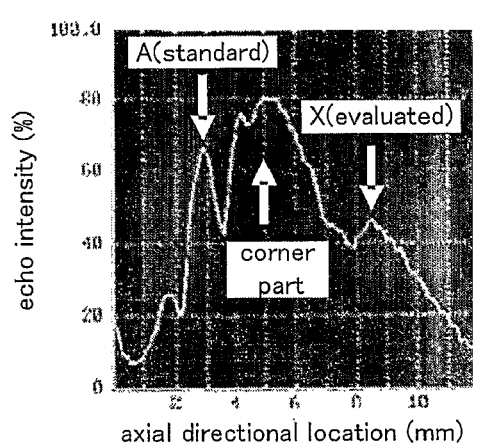
Figure 13B:
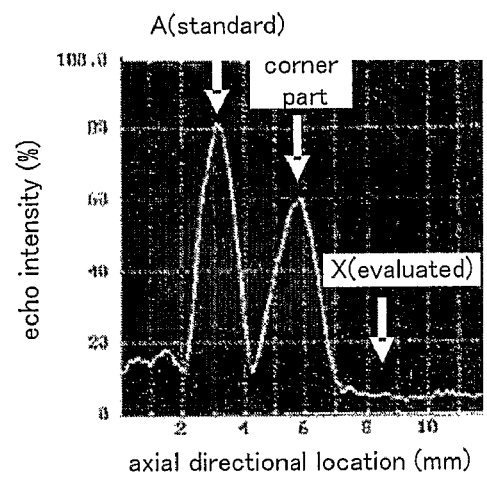
Figure 14:
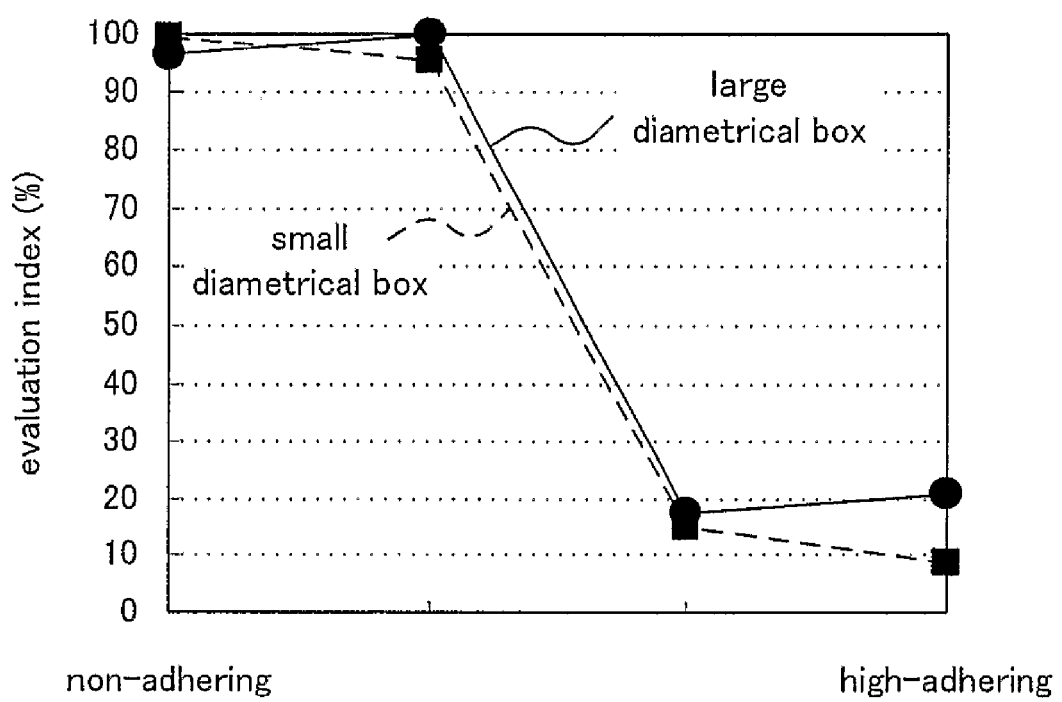
Figure 15:
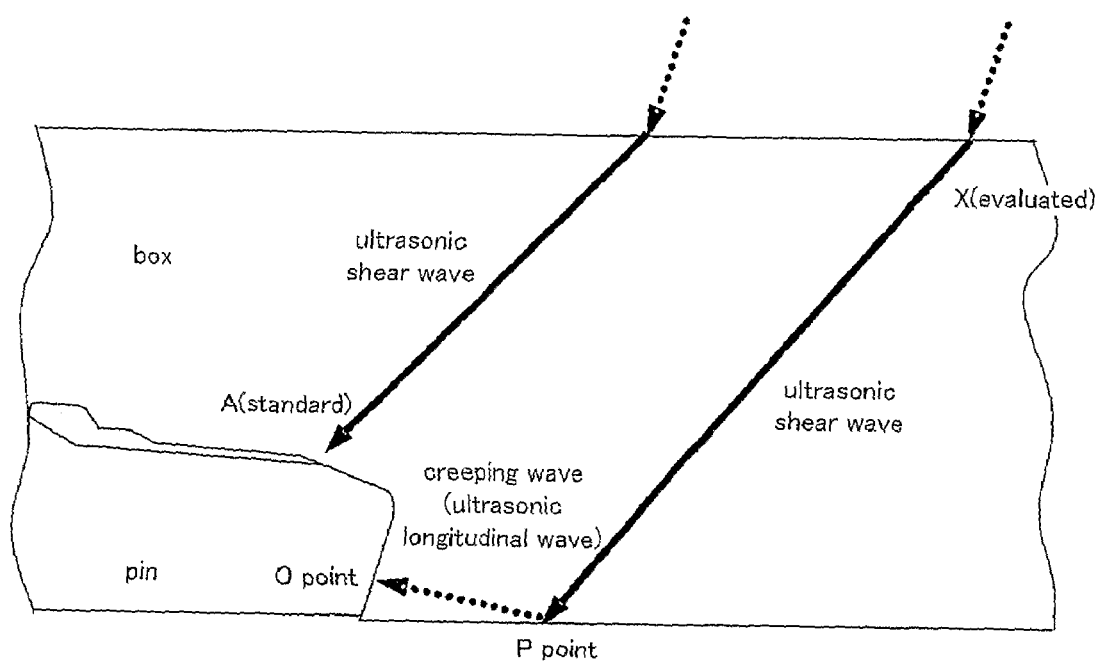
Figure 16A:
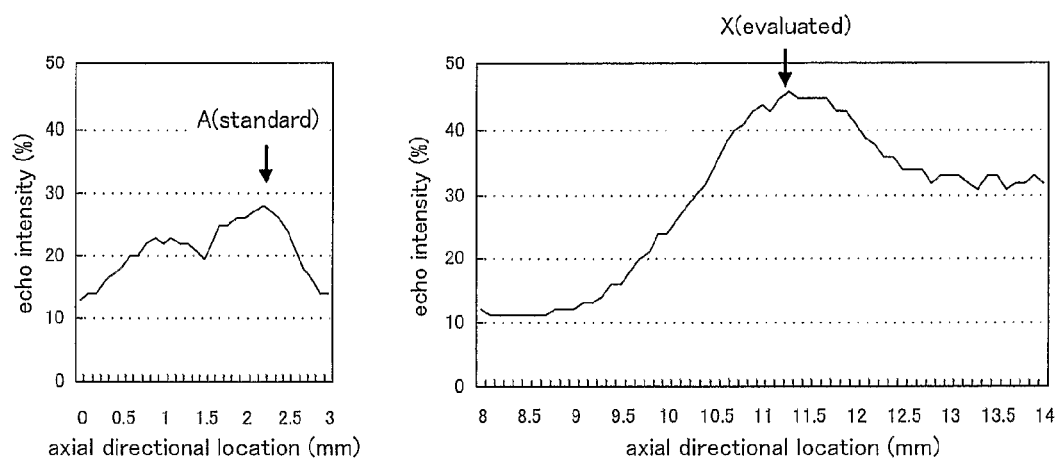
Figure 16B:
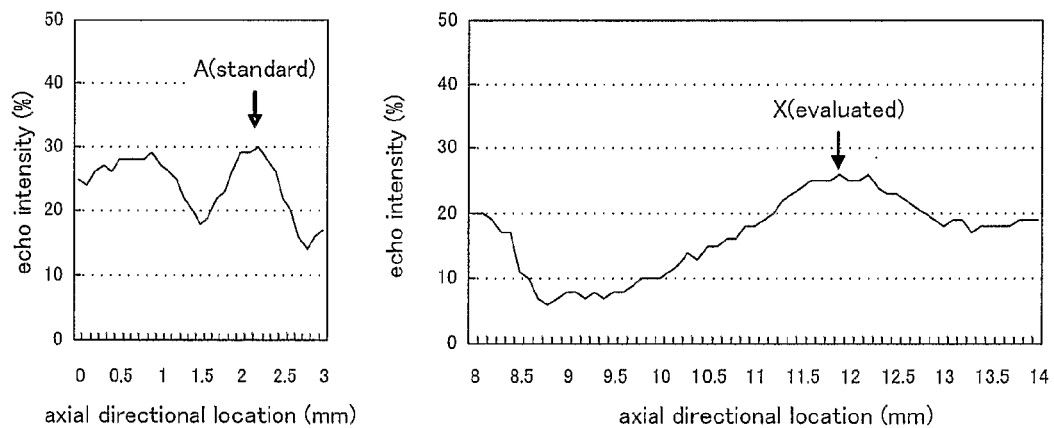
Figure 17:
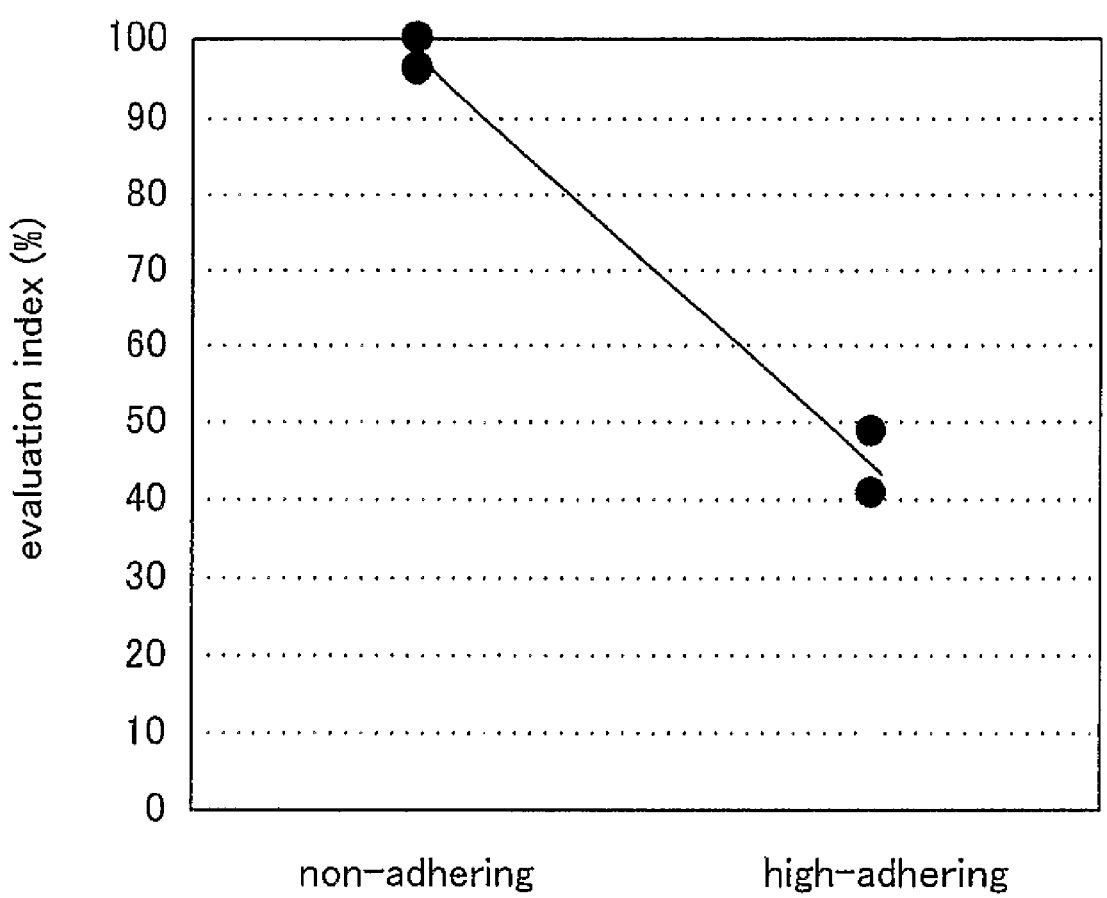
Figure 18:
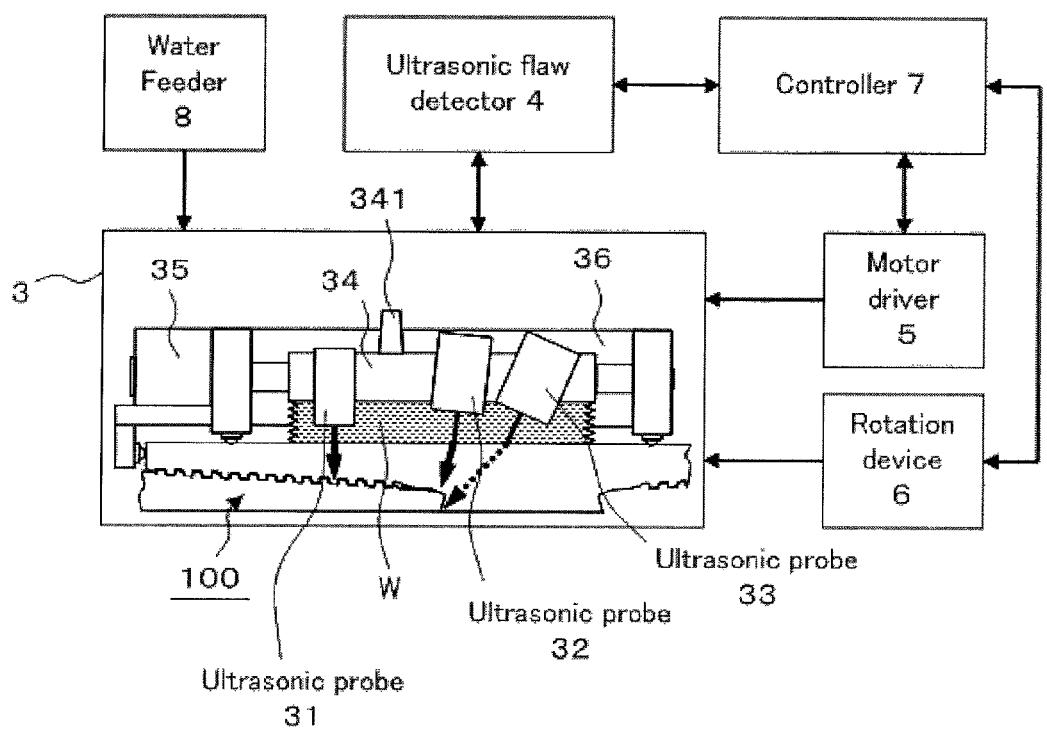
Figure 19:
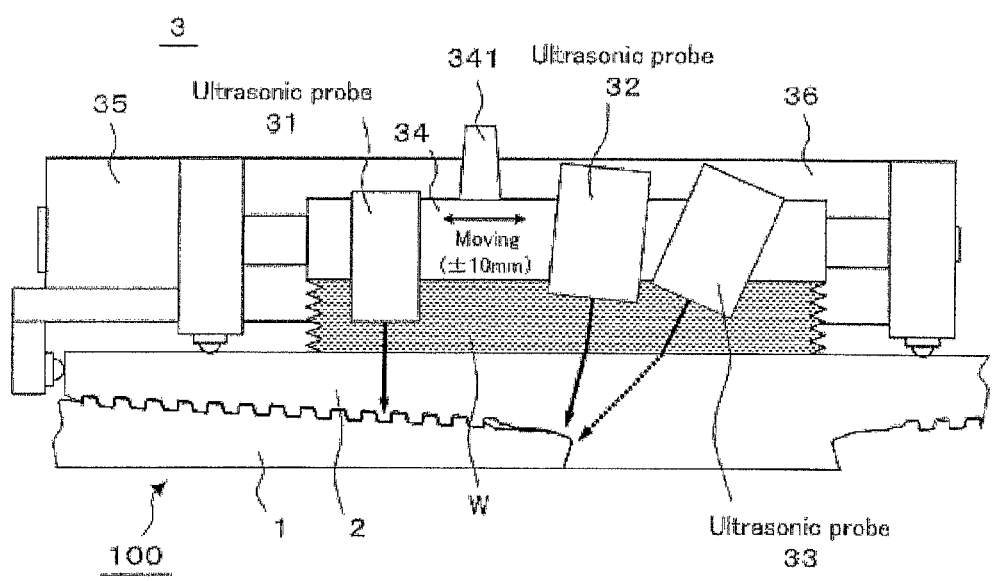
Figure 20A:
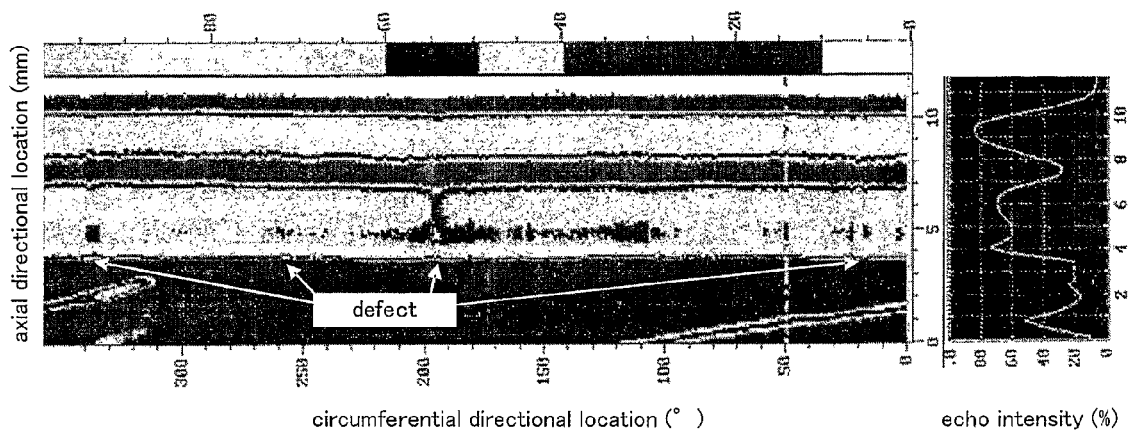
Figure 20B:
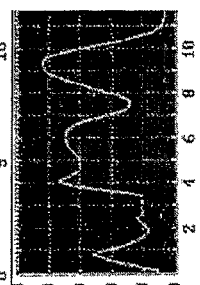
Figure 21:
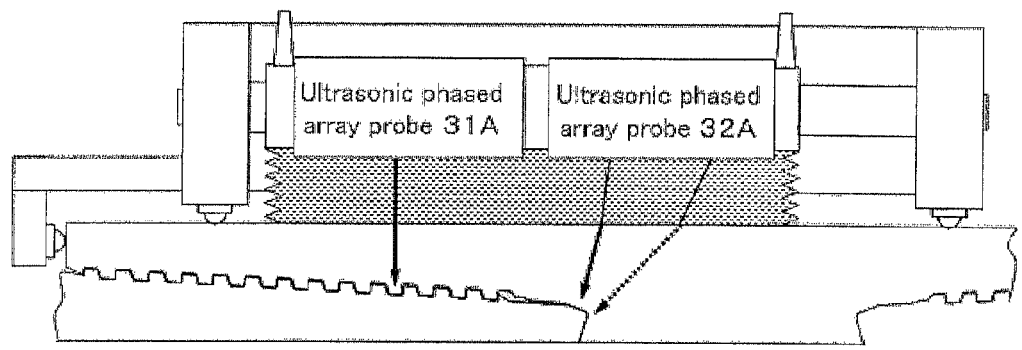
Figure 22A:
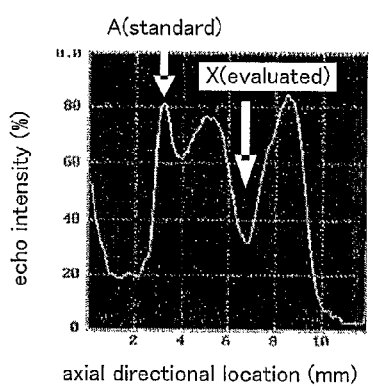
Figure 22B:
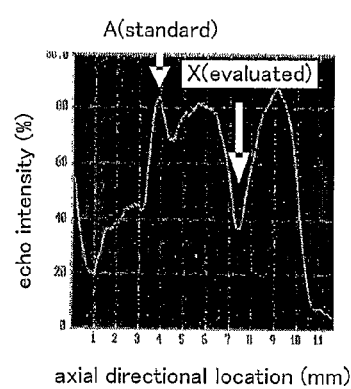
Figure 22C:
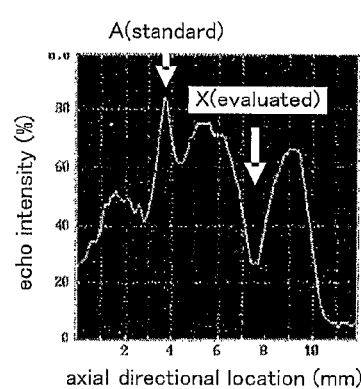
Figure 23:
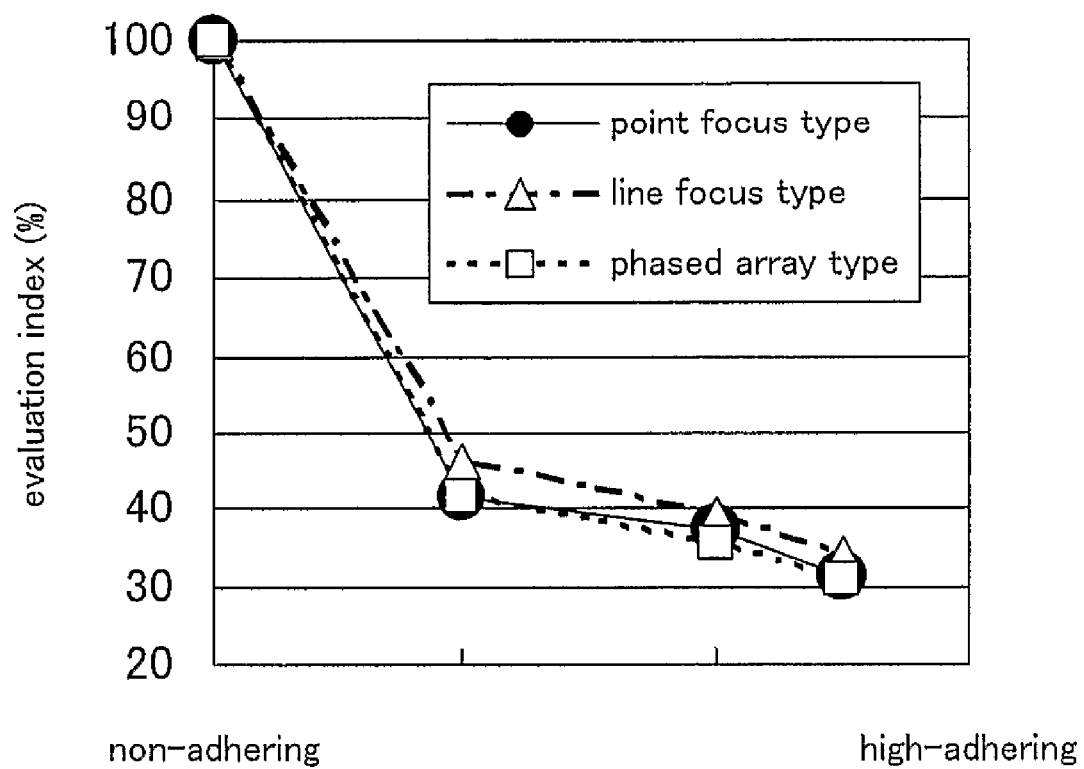

FIG. 3 (FIG. 3A, FIG. 3B, FIG. 3C, FIG. 3D and FIG. 3E) illustrates an example of a result of calculating a contact surface pressure of each part when each part of a pin and each part of a box forming a threaded joint are fastened adhering tightly with each other by a numeric simulation;

FIG. 4 (FIG. 4A and FIG. 4B) is a graph showing an example of an axial directional distribution of an echo intensity that is obtained with respect to an internal thread part of a box;

FIG. 5 (FIG. 5A and FIG. 5B) is a graph showing an example of an axial directional distribution of an echo intensity that is obtained with respect to a metal seal part of the box;

FIG. 6 (FIG. 6A and FIG. 6B) is a graph showing an example of an axial directional distribution of an echo intensity that is obtained for a shoulder part of the box;

FIG. 7 is an explanatory view for explaining a specific example of an evaluating method when a part to be evaluated is an internal thread part;

FIG. 8 is an explanatory view for explaining a specific example of the evaluating method when the part to be evaluated is a metal seal part;

FIG. 9 is an explanatory view for explaining a specific example of the evaluating method when the part to be evaluated is a shoulder part;

FIG. 10 (FIG. 10A, FIG. 10B and FIG. 10C) is a graph showing an example of a result of evaluating variation of an evaluation index when an adhering state between each part of the pin and each part of the box is changed;

FIG. 11 illustrates a result of evaluating an effect of a frequency on variation of the evaluation index;

FIG. 12 is an explanatory view for explaining a specific example of other evaluating method when the part to be evaluated is a shoulder part;

FIG. 13 (FIG. 13A and FIG. 13B) is a graph showing an example of an axial directional distribution of an echo intensity that is obtained with respect to the shoulder part of the box according to the method shown in FIG. 12;

FIG. 14 is a graph showing an example of a result of evaluating variation of an evaluation index when an adhering state between the shoulder part of the pin and the shoulder part of the box is changed according to the method shown in FIG. 12;

FIG. 15 is an explanatory view for explaining a specific example of further other evaluating method when the part to be evaluated is a shoulder part;

FIG. 16 (FIG. 16A and FIG. 16B) is a graph showing an example of an axial directional distribution of an echo intensity that is obtained with respect to the shoulder part of the box according to the method shown in FIG. 15;

FIG. 17 is a graph showing an example of a result of evaluating variation of an evaluation index when an adhering state between the shoulder part of the pin and the shoulder part of the box is changed according to the method shown in FIG. 15;

FIG. 18 is a block diagram schematically showing an entire constitution of an evaluating apparatus for carrying out an evaluating method according to the present invention;

FIG. 19 is a schematic block diagram of an ultrasonic wave scanner forming the evaluating apparatus;

FIG. 20 (FIG. 20A and FIG. 20B) illustrates an example of a result of measuring an echo intensity of the metal seal part in an adhering state by using the evaluating apparatus;

FIG. 21 is a schematic block diagram of an ultrasonic wave scanner according to other example;

FIG. 22 (FIG. 22A, FIG. 22B and FIG. 22C) is a graph showing an example of an axial directional distribution of an echo intensity that is obtained with respect to the metal seal part in the adhering state by measurement using various ultrasonic probes; and FIG. 23 is a graph showing an example of a result of evaluating variation of an evaluation index when an adhering state between the metal seal part of the pin and the metal seal part of the box is changed in measurement using various ultrasonic probes.

DETAILED DESCRIPTION OF THE PREFERRED EMBODIMENTS

Hereinafter, with reference to the attached drawings, an embodiment of a method for evaluating a fastening state of a threaded joint of pipes according to the present invention will be described.

At first, the knowledge that is obtained by the inventors of the present invention in the process of making the present invention will be described in detail.

Figure 1:
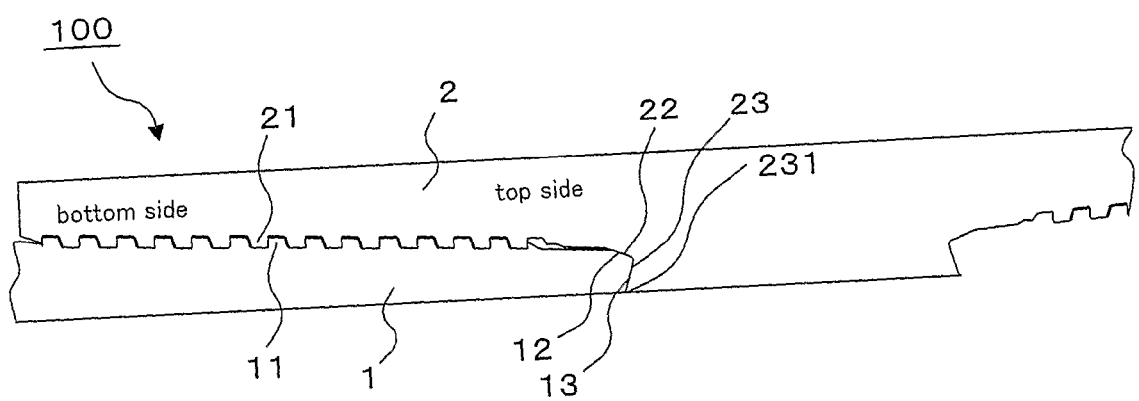
FIG. 1 is a cross sectional view in an axial direction that schematically illustrates a general structure of a threaded joint.
Figure 2:
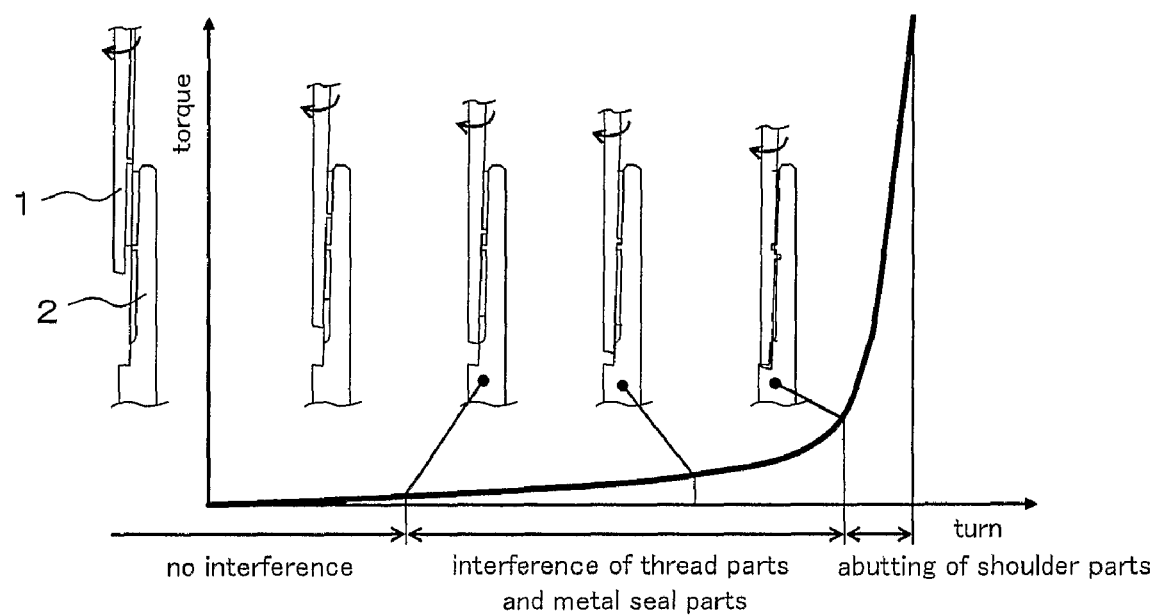
FIG. 2 is an explanatory view for explaining a conventional method for evaluating a fastening state of a threaded joint.

The inventors of the present invention evaluated a contact surface pressure of each part generated when respective parts of a pin 1 (an external thread part 11, a metal seal part 12, and a shoulder part 13) and respective parts (an internal thread part 21, a metal seal part 22, and a shoulder part 23) of a box 2 forming a threaded joint 100 shown in FIG. 1 adhere tightly with each other.

FIG. 3 illustrates an example of a result of calculating a contact surface pressure of each part when each part of a pin and each part of a box forming a threaded joint are fastened adhering tightly with each other by a numeric simulation. Specifically, setting a condition that the external diameter of a screw root of the external thread part 11 is slightly larger than the internal diameter of a screw head of the internal thread part 21, setting a condition that the external diameter of the metal seal part 12 is slightly larger than the internal diameter of the metal seal part 22, and setting a condition that the shoulder part 13 is further screwed toward the shoulder part 23 from the position where the shoulder part 13 abuts against the shoulder part 23 at a first time, a numeric simulation was carried out. FIG. 3A is a view showing a model of a threaded joint that is used for a numeric simulation, FIG. 3B is a graph showing a contact surface pressure between the external thread part 11 and the internal thread part 21, FIG. 3C is a view partially enlarging a model of a threaded joint that is used for a numeric simulation, FIG. 3D is a graph showing a contact surface pressure between the metal seal parts 12, 22, and FIG. 3E is a graph showing a contact surface pressure between the shoulder parts 13, 23. In FIG. 3A and FIG. 3B, lateral axes coincide with each other, in FIG. 3C and FIG. 3D, lateral axes coincide with each other, and in FIG. 3C and FIG. 3E, longitudinal axes coincide with each other.

From a result of a numeric simulation shown in FIG. 3, the knowledge from the following (A) to (E) have been obtained.

(A) The contact surface pressure between the external thread part 11 and the internal thread part 21 is locally higher on the location equivalent to a screw head that is a third from the top side of the internal thread part 21 (a right side of a page space), however, the calculation result of the contact surface pressure is lower right and left of that location because a peak of the contact surface pressure generated by fitting with each other may appear in the vicinity of the end of a fitting part when a wide range of the members including the thread parts is evenly fitted in a general case.

(B) The contact surface pressure between the metal seal part 12 and the metal seal part 22 is locally higher on the location between a center portion and an end portion on the bottom side (near the thread parts 11, 21), however, the calculation result of the contact surface pressure is lower on other locations because, as a result of the fact that the metal seal part 12 is deformed so as to bow (bend and contract a diameter) since the external diameter of the metal seal part 12 is slightly larger than the internal diameter of the metal seal part 22 (namely, the interference margin is provided), a slope of the seal face of the metal seal part 12 and a slope of the seal face of the metal seal part 22 do not coincide with each other and the location between the center portion and the end portion on the bottom side (near the thread parts 11, 21) of the metal seal part 12 strongly contacts the metal seal part 22.

(C) The contact surface pressure between the shoulder part 13 and the shoulder part 23 is locally higher on the location near the metal seal parts 12, 22, however, the calculation result of the contact surface pressure is also locally higher near the corner part because, as described above, the location near the metal seal parts 12, 22 of the shoulder part 13 strongly contact the shoulder part 23 as the metal seal part 12 is deformed so as to bow (bend and contract a diameter) and a peak of the contact surface pressure appears in the vicinity of the end of the fitting part.

(D) Further, in the case of carrying out a numeric simulation setting a condition such that each part of the pin and each part of the box do not adhere tightly with each other (specifically, a condition such that the external diameter of the screw root of the external thread part 11 is made smaller than the internal diameter of the screw head of the internal thread part 21, the external diameter of the metal seal part 12 is made smaller than the internal diameter of the metal seal part 22, and the shoulder part 13 does not abut against the shoulder part 23), a phenomenon such that the contact surface pressure is locally higher does not occur.

(E) From the above-described results (A) to (D), it has been found that the contact surface pressure between each part of the pin and each part of the box is changed depending on the fastening state of these respective parts. Specifically, the contact surface pressure may be higher with respective parts of the pin and respective parts of the box adhering together with each other as compared to the case that they do not adhere together with each other. In addition, it is found that change of the contact surface pressure is not even across the entire area of respective parts and the contact surface pressure is locally changed along the axial direction of the threaded joint. Specifically, when respective parts adhere together with each other, as compared to the case that they do not adhere together with each other, the contact surface pressure may be locally higher.

Next, the inventors of the present invention have conducted a test such that an ultrasonic wave is transmitted and received to and from each part of the box 2 so as to evaluate the axial directional distribution of the echo intensity obtained when the location where the ultrasonic wave is transmitted and received is scanned in the axial direction of the threaded joint 100 with respect to each of the case that respective parts of a pin 1 (an external thread part 11, a metal seal part 12, and a shoulder part 13) and respective parts (an internal thread part 21, a metal seal part 22, and a shoulder part 23) of a box 2 forming a threaded joint 100 shown in FIG. 1 adhere tightly with each other and the case that they do not adhere tightly with each other. Then, they obtained the following knowledge (a) to (d).

(a) At first, the inventors of the present invention vertically transmit and receive the ultrasonic wave to and from the internal thread part 21 of the box (the external diameter: about 150 mm, the internal diameter: about 125 mm) so as to focus the ultrasonic wave on an apex of the screw head of the internal thread part 21 by using an ultrasonic immersion probe (a frequency: 3.5 MHz, a transducer diameter: about 13 mm, a focal distance: about 38 mm, point focus probe), and then, they evaluated the axial directional distribution of the echo intensity that is obtained when the transmission and reception position of this ultrasonic wave is scanned in the axial direction of the threaded joint 100.

FIG. 4 is a graph showing an example of an axial directional distribution of an echo intensity that is obtained with respect to the internal thread part 21 of the box 2. FIG. 4A shows an echo intensity in the case that the internal thread part 21 of the box 2 and the external thread part 11 of the pin 1 do not adhere tightly with each other (the case that the external diameter of the screw root of the external thread part 11 is made smaller than the internal diameter of the screw head of the internal thread part 21), and FIG. 4B shows an echo intensity in the case that the internal thread part 21 of the box 2 and the external thread part 11 of the pin 1 adhere tightly with each other (the case that the external diameter of the screw root of the external thread part 11 is made slightly larger than the internal diameter of the screw head of the internal thread part 21).

The axial directional location represented by an arrow in FIG. 4 is one equivalent to the screw head that is a forth from the top side of the internal thread part 21 (the right side in FIG. 1). As shown in FIG. 4A, in the case of the non-adhering state (namely, in the case that they do not adhere tightly with each other), the echo intensity (a positive peak value) on the location represented by the arrow has no large difference from the echo intensities (the positive peak value) in the screw roots of the internal thread part 21 located right and left thereof and the echo intensities (the positive peak value) in the screw heads that are third and fifth from the top side of the internal thread part 21. On the other hand, as shown in FIG. 4B, in the case of the adhering state (namely, in the case that they adhere tightly with each other), the echo intensity on the location represented by the arrow (the positive peak value) is lower as compared to the case that they do not adhere tightly with each other. In addition, the echo intensity (the positive peak value) in the screw roots of the internal thread part 21 located right and left of the location represented by the arrow and the echo intensities (the positive peak value) in the screw heads that are third and fifth from the top side of the internal thread part 21 have no large difference as compared to the case that they do not adhere tightly with each other. In other words, when the external thread part 11 and the internal thread part 21 adhere tightly with each other (FIG. 4B), as compared to the case that they do not adhere tightly with each other (FIG. 4A), the echo intensity of the ultrasonic wave is locally higher.

(b) Next, the inventors of the present invention transmit and receive the ultrasonic wave to and from the metal seal part 22 of the box (the external diameter: about 150 mm, the internal diameter: about 125 mm) so as to focus the ultrasonic wave on a center portion of the seal face of the metal seal part 22 by using an ultrasonic immersion probe (a frequency: 5 MHz, a transducer diameter: about 19 mm, a focal distance: about 64 mm, point focus probe), and then, they evaluated the axial directional distribution of the echo intensity that is obtained when the transmission and reception position of this ultrasonic wave is scanned in the axial direction of the threaded joint 100. Further, the angle of the ultrasonic immersion probe is adjusted so that the transmitted ultrasonic wave propagates normal to the seal face of the metal seal part 22.

FIG. 5 is a graph showing an example of an axial directional distribution of an echo intensity that is obtained with respect to the metal seal part 22 of the box 2. FIG. 5A shows an echo intensity in the case that the metal seal part 22 of the box 2 and the metal seal part 12 of the pin 1 do not adhere tightly with each other (the case that the external diameter of the metal seal part 12 is made smaller than the internal diameter of the metal seal part 22), and FIG. 5B shows an echo intensity in the case that the metal seal part 22 of the box 2 and the metal seal part 12 of the pin 1 adhere tightly with each other (the case that the external diameter of the metal seal part 12 is made slightly larger than the internal diameter of the metal seal part 22).

As shown in FIG. 5A, in the case that the metal seal part 22 of the box 2 and the metal seal part 12 of the pin 1 do not adhere tightly with each other, there is small variation of the echo intensity across the entire area of the metal seal part 22. On the contrary, as shown in FIG. 5B, in the case that the metal seal part 22 of the box 2 and the metal seal part 12 of the pin 1 adhere tightly with each other, the echo intensity received from the metal seal part 22 is locally lower. In other words, when the metal seal part 12 and the metal seal part 22 adhere tightly with each other (FIG. 5B), the echo intensity of the ultrasonic wave is locally lower as compared to the case that they do not adhere tightly with each other (FIG. 5A).

(c) Further, the inventors of the present invention transmit and receive the ultrasonic wave to and from the shoulder part 23 of the box (the external diameter: about 150 mm, the internal diameter: about 125 mm)so as to focus the ultrasonic wave on a corner part 231 of the shoulder part 23 by using an ultrasonic immersion probe (a frequency: 5 MHz, a transducer diameter: about 19 mm, a focal distance: about 64 mm, point focus probe), and then, they evaluated the axial directional distribution of the echo intensity that is obtained when the transmission and reception position of this ultrasonic wave is scanned in the axial direction of the threaded joint 100. Further, the angle of the ultrasonic immersion probe is adjusted so that the ultrasonic shear wave having an angle of refraction 40° propagates in the box 2.

FIG. 6 is a graph showing an example of an axial directional distribution of an echo intensity that is obtained for the shoulder part 23 of the box 2. FIG. 6A shows an echo intensity when the shoulder part 23 of the box 2 and the shoulder part 13 of the pin 1 do not adhere tightly with each other (namely, in the case that the shoulder part 13 does not abut against the shoulder part 23), and FIG. 6B shows an echo intensity when the shoulder part 23 of the box 2 and the shoulder part 13 of the pin 1 adhere tightly with each other (namely, in the case that the shoulder part 13 is further screwed toward the shoulder part 23 from the position where the shoulder part 13 abuts against the shoulder part 23 at first).

As shown in FIG. 6A, when the shoulder part 23 of the box 2 and the shoulder part 13 of the pin 1 do no adhere tightly with each other, the echo intensity from the corner part 231 (the intensity of the corner echo) of the shoulder part 23 (see FIG. 1) is higher. On the contrary, as shown in FIG. 6B, when they adhere tightly with each other, the intensity of the corner echo is lower. On the other hand, the echo is obtained also from the end portion on the bottom side of the seal face of the metal seal part 22, however, the echo intensity when they adhere tightly with each other is hardly changed from the echo intensity when they do not adhere tightly with each other. In other words, in the case that the shoulder part 13 adheres tightly with the shoulder part 23 (FIG. 6B), as compared to the case that they do not adhere tightly with each other (FIG. 6A), the echo intensity of the ultrasonic wave is locally lower.

As described above, the inventors of the present invention have known that the contact surface pressure between each part of the pin forming the threaded joint and each part of the box corresponding to this is locally higher along an axial direction of the threaded joint as they adhere tightly with each other (refer to FIG. 3). Then, there is a tendency that the echo intensity of the ultrasonic wave received from the location with a high contact surface pressure is lower than the echo intensity of the ultrasonic wave received from the location with a low contact surface pressure. As a result of this, the inventors have known that the echo intensity of the ultrasonic wave is locally lower (refer to FIG. 4B, FIG. 5B, and FIG. 6B). On the other hand, the inventors have known that there is a tendency that the echo intensity of the ultrasonic wave is made larger across the entire area of each part since there is no location where the contact surface pressure is locally higher on each part of the box in the case that each part of the box does not adhere tightly with each part of the pin (refer to FIG. 4A, FIG. 5A, and FIG. 6A).

The present invention has been completed on the basis of the knowledge of the inventors, and the present invention is characterized by transmitting and receiving ultrasonic waves from and to a plurality of locations along an axial direction of the threaded joint 100 for at least one part among the internal thread part 21, the metal seal part 22, and the shoulder part 23 of the box 2 and good and bad of the fastening state of the threaded joint 100 is determined by comparing the echo intensities detected for the plural locations.

According to the present invention, by comparing the echo intensities on a plurality of locations along the axial direction of the threaded joint 100 for at least one part (the part to be evaluated) among the internal thread part 21, the metal seal part 22, and the shoulder part 23, it is possible to detect whether there is an area where the echo intensity of the ultrasonic wave is locally lower or not on the part to be evaluated. Then, if there is an area where the echo intensity of the ultrasonic wave is locally lower on the part to be evaluated, the part to be evaluated of the box and the part of the pin corresponding to this adhere tightly with each other, so that it is possible to determine that this is a good fastening state. On the other hand, if there is no area where the echo intensity of the ultrasonic wave is locally lower on the part to be evaluated, the part to be evaluated of the box and the part of the pin corresponding to this do not adhere tightly with each other, and it is possible to determine that the fastening state is not good (including the case that fastening has not been completed).

Hereinafter, a specific example of an evaluating method according to the present invention (namely, a specific example of a comparing method of echo intensities for a plurality of locations in the part to be evaluated) will be described.

FIG. 7 is an explanatory view for explaining a specific example of an evaluating method when a part to be evaluated is the internal thread part 21. As shown in FIG. 7, in order to evaluate the fastening state of the internal thread part 21 and the external thread part 11 corresponding to this, an echo intensity (X) of an echo having the minimum echo intensity (a positive peak value) among the axial directional distribution of the echo intensity obtained by scanning an ultrasonic wave across a plurality of screw heads of the internal thread part 21 and echo intensities (A, B) adjacent to this are read. The echo intensities (A, B) are used as an echo intensity that is a standard hardly change even if the fastening states of the thread parts 11 and 21 are changed. Then, making these ratios (X/(A+B), X/A, or X/B) into an evaluation index, this evaluation index is compared to a predetermined threshold value (Th). Then, if the evaluation index is not more than the threshold value, the fastening state may be determined to be good, and if the evaluation index exceeds the threshold value, the fastening state may be determined to be not good.

FIG. 8 is an explanatory view for explaining a specific example of the evaluating method when the part to be evaluated is the metal seal part 22. As shown in FIG. 8, in order to evaluate the fastening state between the metal seal part 22 and the metal seal part 12 corresponding to this, an echo intensity (X) in the vicinity of the center portion of the seal face of the metal seal part 22 and an echo intensity (A) of the end portion on the bottom side of the seal face are read in the axial directional distribution of the echo intensity that is obtained by scanning an ultrasonic probe in the area including the metal seal part 22. Specifically, reading the minimum echo intensity from among the echo intensities on the axial directional location in a predetermined range that may coincide with or be adjacent to the vicinity of the center portion of the seal face of the metal seal part 22, this minimum echo intensity is defined as X. On the other hand, reading the maximum echo intensity from among the echo intensities on the axial directional location in a predetermined range that may coincide with or be adjacent to the end portion on the bottom side of the seal face, this maximum echo intensity is defined as A. The echo intensity (A) is used as an echo intensity that is a standard hardly changed even if the fastening states of the metal seal parts 12, 22 are changed. Then, defining a ratio of these echo intensities (X/A) as an evaluation index and comparing this evaluation index with a predetermined threshold value (Th). Then, if the evaluation index is not more than the threshold value, it may be determined that the fastening state is good, and if the evaluation index exceeds the threshold value, it may be determined that the fastening state is not good.

FIG. 9 is an explanatory view for explaining a specific example of the evaluating method when the part to be evaluated is the shoulder part 23. As shown in FIG. 9, in order to evaluate the fastening state between the shoulder part 23 and the shoulder part 13 corresponding to this, a corner echo intensity (X) of the corner part 231 and an echo intensity (A) of the end portion on the bottom side of the seal face are read in the axial directional distribution of the echo intensity that is obtained by scanning an ultrasonic shear wave having an angle of refraction in the range of about 35° to 45° in the area including from the corner part 231 of the shoulder part 23 to the end portion on the bottom side of the seal face of the metal seal part 22. Specifically, reading the maximum echo intensity from among the echo intensities on the axial directional location in a predetermined range that may coincide with or be adjacent to the corner part 231, this maximum echo intensity is defined as X, and on the other hand, reading the maximum echo intensity from among the echo intensities on the axial directional location in a predetermined range that may coincide with or be adjacent to the end portion at the bottom side of the seal face, this maximum echo intensity is defined as A. The echo intensity (A) is used as an echo intensity that is a standard hardly changed even if the fastening states of the shoulder parts 13, 23 are changed. Then, defining a ratio of these echo intensities (X/A) as an evaluation index and comparing this evaluation index with a predetermined threshold value (Th). Then, if the evaluation index is not more than the threshold value, it may be determined that the fastening state is good, and if the evaluation index exceeds the threshold value, it may be determined that the fastening state is not good.

FIG. 10 is a graph showing an example of a result of evaluating variation of an evaluation index when an adhering state between each part of the pin and each part of the box is changed. FIG. 10A shows the case that the part to be evaluated is the internal thread part 21. For this evaluation, an ultrasonic probe that is the same as that used for the evaluation test having a result shown in FIG. 4 is used. FIG. 10B shows the case that the part to be evaluated is the metal seal part 22. For this evaluation, an ultrasonic probe that is the same as that used for the evaluation test having a result shown in FIG. 5 is used. FIG. 10C shows the case that the part to be evaluated is the shoulder part 23. For this evaluation, an ultrasonic probe that is the same as that used for the evaluation test having a result shown in FIG. 6 is used. A lateral axis of FIG. 10A is a value that is equivalent to the interference margins of the thread parts 11 and 21. In addition, a lateral axis of FIG. 10B is a value that is equivalent to the interference margins of the metal seal parts 12 and 22. Further, a lateral axis of FIG. 10C is a value that is equivalent to the screwing amount when the shoulder part 13 is further screwed toward the shoulder part 23 from the position where the shoulder part 13 abuts against the shoulder part 23 at first.

As shown in FIG. 10, the higher the adhering state between each part of the pin and each part of the box is made, the lower the value of the evaluation index is. This means that an evaluating method, as described above, to determine that the fastening state is good if the evaluation index is not more than a predetermined threshold value and to determine that the fastening state is not good if the evaluation index exceeds the predetermined threshold value is appropriate. Further, the evaluating method according to the present invention is not only used for evaluating good and bad of the fastening state of the threaded joint 100 after the fastening operation is terminated but also can be applied to the method for fastening the threaded joint itself. In other words, in the fastening process of the threaded joint, monitoring variation of the evaluation index as shown in FIG. 10, in the stage that the evaluation index is not more than a predetermined threshold value (for example, 50%), the fastening of the threaded joint can be also terminated.

Further, with respect to the case that the part to be evaluated is the internal thread part 21 (FIG. 10A), changing a frequency of an ultrasonic wave (a test frequency) to be transmitted and received, an effect from the frequency on variation of the evaluation index is evaluated. FIG. 11 shows a result of evaluation.

As shown in FIG. 11, in the case that the frequency is made into a high frequency about 30 MHz, the value of the evaluation index is not largely made lower, even if the adhering state of the thread parts 11 and 21 is made higher. Accordingly, it is preferable that the frequency of the ultrasonic wave to be transmitted and received is set to be not more than 25 MHz (more preferably, not more than 5 MHz).

As shown in FIG. 12, due to an effect of a dimension tolerance or the like, the internal diameter of the box 2 is made smaller than the internal diameter of the pin, so that there is a possibility that a very small difference is found on the internal diametrical sides of the shoulder parts 12 and 23. When this difference exists, the above-described corner echo intensity (X) of the corner part 231 may include an echo intensity that is reflected from the difference, so that there is a possibility that the fastening states of the shoulder parts 13 and 23 cannot be appropriately evaluated.

In order to avoid this, as shown in FIG. 12, a method using mode conversion of an ultrasonic wave can be employed. Specifically, as a result of concentration of consideration, the inventors found that there was a propagation path of an ultrasonic wave, in which the ultrasonic shear wave propagated from the outer surface of the box 2 was reflected on a P point of the inner surface of the box 2, and this ultrasonic shear wave was converted into an ultrasonic longitudinal wave when this hits an O point of the shoulder part 23 to be reflected and received by the ultrasonic probe, as shown in FIG. 12. This propagation path is not routed through the above-described difference, so that, if the echo intensity of the mode-converted ultrasonic wave is used as the evaluation index in place of the above-described corner echo intensity, the fastening states of the shoulder parts 13 and 23 can be appropriately evaluated without having an effect of the difference.

FIG. 13 is a graph showing an example of an axial directional distribution of an echo intensity that is obtained when the ultrasonic wave is transmitted and received so as to focus the ultrasonic wave on the inner surface of the box by using an ultrasonic immersion probe (a frequency: 5 MHz, a transducer diameter: about 19 mm, a focal distance: about 64 mm, point focus probe) with respect to the shoulder part 23 of the box (the external diameter: about 80 mm, the internal diameter: about 60 mm) having a difference on its internal diametrical side and the transmission and reception position of this ultrasonic wave is scanned in the axial direction of the threaded joint 100. FIG. 13A shows the echo intensity when the shoulder part 23 of the box 2 and the shoulder part 13 of the pin 1 do not adhere tightly with each other (namely, in the case that the shoulder part 13 does not abut against the shoulder part 23), and FIG. 13B shows the echo intensity when the shoulder part 23 of the box 2 and the shoulder part 23 of the pin 1 adhere tightly with each other (namely, in the case that the shoulder part 13 is further screwed toward the shoulder part 23 from the position where the shoulder part 13 abuts against the shoulder part 23 at first).

As shown in FIG. 13A, in the case that the shoulder part 23 of the box 2 and the shoulder part 13 of the pin 1 do not adhere tightly with each other, the echo to be received by the ultrasonic probe by conversion of a mode (hereinafter, referred to as a mode conversion echo) can be confirmed. On the contrary, as shown in FIG. 13B, when they adhere tightly with each other, the mode conversion echo is not received. Accordingly, defining a ratio (X/A) between the echo intensity (X) of a mode conversion echo and the echo intensity (A) of the end portion on the bottom side of the seal face as an evaluation index and comparing this evaluation index with a predetermined threshold value (Th). Then, if the evaluation index is not more than the threshold value, it can be determined that the fastening state is good, and if the evaluation index exceeds the threshold value, it can be determined that the fastening state is not good. Further, reading of the intensity (X) of the mode conversion echo may be carried out as follows. In other words, reading the maximum echo intensity from among the echo intensities on the axial directional location in a predetermined range that may coincide with or be adjacent to a point where the ultrasonic shear wave propagated from the outer surface of the box (for example, a P point shown in FIG. 12), this intensity may be defined as X.

FIG. 14 is a graph showing an example of a result of evaluating variation of an evaluation index (X/A) when an adhering state between the shoulder part 13 of the pin and the shoulder part 23 of the box is changed by using the ultrasonic probe as same as the above with respect to each shoulder part 23 of the large diametrical box (the external diameter: about 190 mm, the internal diameter: about 160 mm) and the small diametrical box (the external diameter: about 80 mm, the internal diameter: about 60 mm) having a difference in its internal diametrical side, respectively. Further, the lateral axis of FIG. 14 is a value that is equivalent to the screwing amount when the shoulder part 13 is further screwed toward the shoulder part 23 from the position where the shoulder part 13 abuts against the shoulder part 23 at first.

As shown in FIG. 14, even if the box is any of the large diametrical box and the small diametrical box, it is known that, the higher the adhering state between the shoulder parts 13 and 23 is made, it is inclined that the value of the evaluation index represented by a ratio between the intensity (X) of the mode conversion echo and the echo intensity (A) of the end portion on the bottom side of the seal face is decreased. As a result, as described above, comparing this evaluation index with a predetermined threshold value (Th), if the evaluation index is not more than the threshold value, it can be determined that the fastening state is good, and if the evaluation index exceeds the threshold value, it can be determined that the fastening state is not good.

In addition, in order to avoid the effect of the difference located on the internal diametrical side of the shoulder parts 13 and 23, as shown in FIG. 15, a method using a creeping wave can be also employed. As shown in FIG. 15, when the ultrasonic shear wave propagated from the outer surface of the box 2 is reflected on the P point of the inner surface of the box 2, a secondary creeping wave is generated. As a result of concentration of consideration, the inventors found that there was a propagation path of an ultrasonic wave, in which this secondary creeping wave propagates to the shoulder part 23 at a substantially vertical angle and when the shoulder parts 13 and 23 do not adhere tightly with each other, the secondary creeping wave is reflected on the shoulder part 23 to be received by the ultrasonic probe being routed through an original path. Since this propagation path is not routed through the difference, if the echo intensity of the secondary creeping wave is used as the evaluation index in place of the above-described corner echo intensity, without having the effect of the difference, the fastening state between the shoulder parts 13 and 23 can be appropriately evaluated.

FIG. 16 is a graph showing an example of an axial directional distribution of an echo intensity that is obtained when transmitting and receiving an ultrasonic wave so as to focus the ultrasonic wave in the vicinity of the inner surface of the box by using an ultrasonic immersion probe (a frequency: 5 MHz, a transducer diameter: about 19 mm, a focal distance: about 64 mm, point focus probe) and scanning the transmission and reception position of the ultrasonic wave in the axial direction of the threaded joint 100 about the shoulder part 23 of the box (the external diameter: about 190 mm, the internal diameter: about 160 mm) having the difference on the interior diametrical side. FIG. 16A shows the echo intensity when the shoulder part 23 of the box 2 and the shoulder part 13 of the pin 1 do not adhere tightly with each other (namely, in the case that the shoulder part 13 does not abut against the shoulder part 23), and FIG. 16B shows the echo intensity when the shoulder part 23 of the box 2 and the shoulder part 23 of the pin 1 adhere tightly with each other (namely, in the case that the shoulder part 13 is further screwed toward the shoulder part 23 from the position where the shoulder part 13 abuts against the shoulder part 23 at first).

As shown in FIG. 16A, in the case of the non-adhering state, the intensity of the echo to be received by the ultrasonic probe as the secondary creeping wave (hereinafter, referred to as a secondary creeping wave echo) is increased. On the contrary, as shown in FIG. 16B, in the case of the adhering state, the intensity of the secondary creeping wave echo is made lower. Accordingly, defining a ratio (X/A) between the intensity (X) of the secondary creeping wave echo and the echo intensity (A) of the end portion on the bottom side of the seal face as an evaluation index and comparing this evaluation index with a predetermined threshold value (Th), if the evaluation index is not more than the threshold value, it can be determined that the fastening state is good, and if the evaluation index exceeds the threshold value, it can be determined that the fastening state is not good. Further, reading of the intensity (X) of the secondary creeping wave echo may be carried out as follows. In other words, reading the maximum echo intensity from among the echo intensities on the axial directional location in a predetermined range that may coincide with or be adjacent to a point where the ultrasonic shear wave propagated from the outer surface of the box (for example, a P point shown in FIG. 12), this intensity may be defined as X.

FIG. 17 is a graph showing an example of a result of evaluating variation of an evaluation index (X/A) when an adhering state between the shoulder part 13 of the pin and the shoulder part 23 of the box is changed by using the ultrasonic probe as same as the above with respect to the shoulder part 23 of the box (the external diameter: about 190 mm, the internal diameter: about 160 mm) having a difference in its internal diametrical side. Further, the lateral axis of FIG. 17 is a value that is equivalent to the screwing amount when the shoulder part 13 is further screwed toward the shoulder part 23 from the position where the shoulder part 13 abuts against the shoulder part 23 at first.

As shown in FIG. 17, if the adhering state between the shoulder parts 13 and 23 is made higher, it is found that the value of the evaluation index represented by a ratio between the intensity (X) of the secondary creeping wave echo and the echo intensity (A) of the end portion on the bottom side of the seal face is made lower. Accordingly, as described above, comparing this evaluation index with a predetermined threshold value (Th), if the evaluation index is not more than the threshold value, it can be determined that the fastening state is good, and if the evaluation index exceeds the threshold value, it can be determined that the fastening state is not good.

Hereinafter, the specific example of an evaluating apparatus for carrying out a method for evaluating a fastening state of a threaded joint according to the present invention will be described.

FIG. 18 is a block diagram schematically showing an entire constitution of an evaluating apparatus. FIG. 19 is a schematic block diagram of an ultrasonic wave scanner forming the evaluating apparatus.

As shown in FIG. 18 and FIG. 19, an evaluating apparatus 200 according to the present embodiment is provided with an ultrasonic wave scanner 3 for scanning an ultrasonic wave along the axial direction of the threaded joint 100, an ultrasonic flaw detector 4 for controlling transmission and reception of the ultrasonic waves from ultrasonic probes 31, 32, and 33 provided to the ultrasonic wave scanner 3, a motor driver 5 for driving a motor 35 provided to the ultrasonic wave scanner 3, a rotation device 6 for scanning the ultrasonic wave scanner 3 along a circumferential direction of the threaded joint 100 or rotating the threaded joint 100 in a circumferential direction, a controller 7 for controlling the ultrasonic flaw detector 4, a motor driver 5, and the rotation device 6, and a water feeder 8 for feeding water W as a contact medium of the ultrasonic wave.

The ultrasonic wave scanner 3 is provided with the ultrasonic probe 31 for evaluating the fastening state between thread parts 11 and 12, the ultrasonic probe 32 for evaluating the fastening state between metal seal parts 12 and 22, and the ultrasonic probe 33 for evaluating the fastening state between the shoulder parts 13 and 23. As the ultrasonic probe 31, the ultrasonic probe 32, and the ultrasonic probe 33, ultrasonic probe as same as that used for an evaluation test that obtains a result shown in FIG. 4, the ultrasonic probe as same as that used for an evaluation test that obtains a result shown in FIG. 5, and the ultrasonic probe as same as that used for an evaluation test that obtains a result shown in FIG. 6 can be used, respectively. Further, it is preferable that a diameter of the focused ultrasonic wave beam (namely, an ultrasonic wave beam diameter on a focal point) is small as much as possible, and it is preferable that this diameter of the ultrasonic probe 31, for example, is not more than the length of the apex of the screw head of the internal thread part 21 (the length along the axial direction of the threaded joint).

The ultrasonic wave scanner 3 is provided with a probe holder 34, a motor 35, and a table 36 on which the probe holder 34 and the motor 35 are attached in addition to the ultrasonic probes 31, 32, and 33.

The ultrasonic probes 31, 32, and 33 are attached to the probe holder 34. The probe holder 34 is also provided with a function for filling water W as a contact medium that is fed from the water feeder 8 and flows from a water feeding port 341 in a gap between the ultrasonic probes 31 to 33 and the outer surface of the box 2 of the threaded joint 100. A rotational motive energy of the motor 35 is transmitted to the probe holder 34 via an appropriate mechanical element for converting this rotational motive energy into a linear motion, and thereby, the probe holder 34 can move along the axial direction of the threaded joint 100. Due to movement of the probe holder 34, ultrasonic probes 31, 32, and 33 attached to the probe holder 34 also move along the axial direction of the threaded joint 100, and thereby, the transmission and reception position of the ultrasonic wave is scanned along the axial direction of the threaded joint 100. In this case, since the table 36 holds the state contacting the threaded joint 100 (the box 2), a distance between the probe holder 34 attached to the table 36 and the outer surface of the box 2, and further, a distance between the ultrasonic probes 31, 32, and 33 and the outer surface of the box 2 can be kept constantly. Then, since the table 36 or the threaded joint 100 are rotated in a circumferential direction by the rotation device 6, it is possible to transmit and receive the ultrasonic wave to and from a plurality of locations in a circumferential direction of the threaded joint 100.

FIG. 20 illustrates an example of a result of measuring an echo intensity of the metal seal part 2 in an adhering state by using the evaluating apparatus 200 having the above-described structure. According to the example shown in FIG. 20, the echo intensity distribution of the all circumference is measured at 12 mm pitches in the axial direction of the threaded joint 100 and 1° pitch in the circumferential direction. FIG. 20A illustrates a C scope that is separated by a color depending on the volume of the echo intensity on each measuring point with a lateral axis in a circumferential direction and a longitudinal axis in an axial direction. FIG. 20B illustrates the axial directional distribution of the echo intensity received from the location of the circumferential direction 50°.

As shown in FIG. 20A, in an area other than the area where there is a defect upon fastening (namely, a defect generated on the outer surface of the box 2 when the box 2 is held by means of a tool upon fastening), the echo intensity that is substantially even in the circumferential direction is obtained. In addition, as shown in FIG. 20B, it is found that the echo intensity is lower on a substantially center portion of the metal seal part in the axial directional distribution of the echo intensity received from the location of a circumferential direction 50°. Further, according to the result shown in FIG. 20, unevenness of the fastening state for the circumferential direction of the threaded joint 100 is not perceived, so that it may be considered that scanning of the ultrasonic wave in the circumferential direction is not necessary. However, in order to carry out strict evaluation, it is preferable to carry out scanning in the circumferential direction, and in consideration of the operational efficiency or the like, the measurement pitch in the circumferential direction is preferably selected, for example, from among 180°, 90°, and 45° or the like.

Further, the ultrasonic wave scanner is not limited to the structure shown in FIG. 13 and for example, the structure including an ultrasonic phased array probe (according to the example shown in FIG. 21, an ultrasonic phased array probe 31A for evaluating the fastening state between the thread parts 11 and 21 and an ultrasonic phased array probe 32A for evaluating the fastening state between the metal seal parts 12 and 22 and for evaluating the fastening state between the shoulder parts 13 and 23) as shown in FIG. 21 can be also employed. Then, by electrically controlling transmission and reception of the ultrasonic wave by means of each transducer of the ultrasonic phased array probes 31A and 32A according to a publicly-known method, the ultrasonic wave to be transmitted and received may be scanned in the axial direction of the threaded joint 100.

The inventors of the present invention conducted a test for evaluating the axial directional distribution of the echo intensity in the metal seal part 22 (refer to FIG. 1) of the box (the external diameter: about 150 mm, the internal diameter: about 125 mm) of the threaded joint 100, using the ultrasonic phased array probe 32A shown in FIG. 21 and using a line-focus ultrasonic probe and a point-focus ultrasonic probe as the ultrasonic probe shown in FIG. 18, respectively.

Specifically, with the metal seal part 22 of the box 2 and the metal seal part 12 of the pin 1 adhering tightly with each other (namely, with the external diameter of the metal seal part 12 being slightly larger than the internal diameter of the metal seal part 22), by using each ultrasonic probe shown in a table 1, the ultrasonic wave is transmitted and received so as to be focused on a center portion of the seal face of the metal seal part 22 and the axial directional distribution of the echo intensity is evaluated, which is obtained when the transmission and reception position of this ultrasonic wave is scanned in the axial direction of the threaded joint 100. The transducer size of the ultrasonic phased array probe 32A shown in the table 1 means that thirty two pieces of the transducer having the size of 0.75 mm along the axial direction of the threaded joint 100 and the size of 10 mm along the circumferential direction are arranged. In addition, an ultrasonic beam size shown in the table 1 is the size of the ultrasonic wave beam on a focal point (a distance between the positions where the intensity is lower than the maximum intensity by 6 dB). The line-focus ultrasonic probe 32 has the ultrasonic wave beam size along the axial direction of the threaded joint 100 of 0.8 mm and the ultrasonic wave beam size along the circumferential direction of 13 mm, and the ultrasonic phased array probe 32A has the ultrasonic wave beam size along the axial direction of the threaded joint 100 of 0.9 mm and the ultrasonic wave beam size along the circumferential direction of 6 mm. Further, with regard to the ultrasonic phased array probe 32A, transmission and reception of the ultrasonic wave by each transducer are electrically controlled so that the transmitted ultrasonic wave propagates normal to the seal face of the metal seal part 22. In addition, each angle of the line-focus and point-focus ultrasonic probes 32 is adjusted so that the transmitted ultrasonic wave propagates normal to the seal face of the metal seal part 22.

TABLE 1

| Ultrasonic probe | Frequency (MHz) | Transducer size (mm) | Focal distance (mm) | Ultrasonic wave beam size (mm) |
| --- | --- | --- | --- | --- |
| Point focus type | 5 | φ19.05 | 63.5 | φ0.9 |
| Line focus type | 5 | φ19.05 | 63.5 | 0.8 × 13 |
| Phased array type | 5 | 0.75 (32 CH) × 10 | 65 | 0.9 × 6 |

FIG. 22 is a graph showing an example of an axial directional distribution of an echo intensity that is obtained with respect to the metal seal part 22 of the box 2. FIG. 22A illustrates the echo intensity when the point-focus ultrasonic probe 32 is used, FIG. 22B illustrates the echo intensity when the line-focus ultrasonic probe 32 is used, and FIG. 22C illustrates the echo intensity when the ultrasonic phased array probe 32A is used. As shown in FIG. 22, also in the case that the line-focus ultrasonic probe 32 and the ultrasonic phased array probe 32A are used, the echo intensity of the ultrasonic wave is locally lower as same as the case of using the point-focus ultrasonic probe 32.

Further, the inventors of the present invention conducted a test for evaluating variation of the evaluation index when the adhering state between the metal seal part 12 of the pin 1 and the metal seal part 22 of the box 2 is changed by using each ultrasonic probe as same as the above-described one. Here, a ratio between the echo intensity (X) in the vicinity of the center portion of the seal face of the metal seal part 22 and the echo intensity (A) of an edge 221 on the bottom side of the metal seal part 22 (refer to FIG. 8) is defined as an evaluation index (refer to FIG. 22). However, as described above with reference to FIG. 8, it is taken for granted that a ratio between the echo intensity in the vicinity of the center part of the seal face of the metal seal part 22 and the echo intensity of an end portion on the bottom side of the seal face can be made into an evaluation index.

FIG. 23 is a graph showing an example of a result of evaluating variation of an evaluation index according to the above-described evaluation test. Further, the lateral axis represents a value that is equivalent to the interference margins of the metal seal parts 12 and 22. As shown in FIG. 23, also when the line-focus ultrasonic probe 32 and the ultrasonic phased array probe 32A are used, as same as the case that the line-focus ultrasonic probe 32 is used, it is found that the evaluation index is varied and the higher the fastening state between the metal seal parts 12 and 22 is made, the lower the value of the evaluation index is.

From a result of the evaluation test that is described with reference to FIG. 22 and FIG. 23, also when the line-focus ultrasonic probe and the ultrasonic phased array probe are used as same as the case of using the point-focus ultrasonic probe, by transmitting and receiving the ultrasonic waves to and from a plurality of locations along the axial direction of the threaded joint 100 and comparing the echo intensity that is detected with respect to these plural locations, it is found that good and bad of the fastening state of the threaded joint 100 can be evaluated.

The invention claimed is:

1. A method for evaluating a fastening state of a threaded joint of pipes or tubes including a pin having an external thread part, a metal seal part, and a shoulder part on an outer peripheral surface, and a box having an internal thread part, a metal seal part, and a shoulder part corresponding to each part of the pin on an inner peripheral surface and being fastened with the pin, the method comprising the steps of:
    transmitting and receiving ultrasonic waves to and from a plurality of locations along a longitudinal axial direction of the threaded joint in at least one of the internal thread part, the metal seal part, and the shoulder part of the box;
    detecting echo intensities for the plurality of locations along the longitudinal axial direction of the threaded joint; and
    comparing the echo intensities detected for the plurality of locations along the longitudinal axial direction of the thread joint with each other to determine whether the fastening state of the threaded joint is good or bad.

2. The method for evaluating the fastening state of the threaded joint of pipes or tubes according to claim 1, wherein the frequency of the ultrasonic wave to be transmitted and received is set to be not more than 25 MHz.

3. The method for evaluating the fastening state of the threaded joint of pipes or tubes according to claim 1, wherein the ultrasonic waves are transmitted and received to and from the plurality of locations along the longitudinal axial direction of the threaded joint in at least one part of the box by relatively moving an ultrasonic probe in the axial direction of the threaded joint.

4. The method for evaluating the fastening state of the threaded joint of pipes or tubes according to claim 1, wherein the ultrasonic waves are transmitted and received to and from the plurality of locations along the longitudinal axial direction of the threaded joint in at least one part of the box by electrically controlling the transmission and reception of the ultrasonic wave by each transducer of an ultrasonic phased array probe in which a plurality of transducers are arrayed in one row.

5. A method of fastening a threaded joint of pipes or tubes, comprising the steps of:
    determining whether the fastening state is good or bad by using the evaluating method according to claim 1 in a fastening process of the threaded joint; and
    terminating the fastening of the threaded joint at a point where the result of determination becomes good.

* * * * *